(12) United States Patent
Harsdorff et al.

(10) Patent No.: US 10,559,184 B2
(45) Date of Patent: *Feb. 11, 2020

(54) MOUNT FOR A PATIENT MONITORING DEVICE

(71) Applicant: Palarum LLC, Lebanon, OH (US)

(72) Inventors: Chris Harsdorff, Lebanon, OH (US); Glenn Wolfe, Dayton, OH (US); Jeffery Steele, Trenton, OH (US)

(73) Assignee: Palarum LLC, Lebanon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/404,813

(22) Filed: May 7, 2019

(65) Prior Publication Data

US 2019/0287374 A1    Sep. 19, 2019

Related U.S. Application Data

(63) Continuation of application No. 15/922,971, filed on Mar. 16, 2018, now Pat. No. 10,325,472.

(51) Int. Cl.
*G08B 21/04* (2006.01)
*A41B 11/00* (2006.01)
(Continued)

(52) U.S. Cl.
CPC .......... *G08B 21/0446* (2013.01); *A41B 11/00* (2013.01); *A61B 5/1117* (2013.01);
(Continued)

(58) Field of Classification Search
CPC .... G08B 21/0446; G08B 21/182; A41B 11/00
(Continued)

(56) References Cited

U.S. PATENT DOCUMENTS 7,559,902 B2    7/2009  Ting et al.
8,140,143 B2    3/2012  Picard et al.
(Continued)

FOREIGN PATENT DOCUMENTS

JP       2011-098214 A    5/2011
WO    WO 2014/093888 A2   6/2014

OTHER PUBLICATIONS

International Search Report for PCT/US2019/02248 dated Mar. 16, 2018.
Written Opinion in PCT/US2019/02248 dated Jun. 20, 2019.

*Primary Examiner* — Kerri L McNally
(74) *Attorney, Agent, or Firm* — Woodard Emhardt Henry Reeves & Wagner LLP

(57) ABSTRACT

A mount for a device configured to monitor the movements or other activities of patient. Aspects include a monitoring unit and base, where the base may further include a pad with one or more pins extending into the base. The pad may be positioned inside a garment worn by a patient, the pins passing through the garment and electrically connecting to circuits in the fabric of the garment (e.g. a sock worn by the patient). The circuits may include sensors which are response to changes in pressure caused by patient movement. Output from the sensors may be carried by the circuits in the garment to the pins in the pad, and from there through the garment and into the base and the monitoring unit for processing and reporting to caregivers as needed.

25 Claims, 9 Drawing Sheets

(51) Int. Cl.
*G08B 21/18* (2006.01)
*A61B 5/11* (2006.01)
*A61B 5/00* (2006.01)
*A41D 13/12* (2006.01)

(52) U.S. Cl.
CPC .......... *A61B 5/6807* (2013.01); *G08B 21/182* (2013.01); *A41B 2500/20* (2013.01); *A41D 13/1281* (2013.01); *A61B 2562/0219* (2013.01)

(58) Field of Classification Search
USPC ..................................................... 340/573.1
See application file for complete search history.

(56) References Cited

U.S. PATENT DOCUMENTS

| | | |
|---|---|---|
| 8,384,551 B2 | 2/2013 | Ross et al. |
| 8,661,915 B2 | 3/2014 | Taylor |
| 8,736,439 B1 | 5/2014 | Shinozuka |
| 8,961,439 B2 | 2/2015 | Yang et al. |
| 9,186,092 B2 | 11/2015 | Mestrovic et al. |
| 9,345,433 B1 | 5/2016 | Shinozuka et al. |
| 9,642,470 B2 | 5/2017 | Taylor |
| 10,325,472 B1* | 6/2019 | Harsdorff ........... G08B 21/0446 |
| 2011/0015498 A1* | 1/2011 | Mestrovic ................ A61B 5/01 600/301 |
| 2012/0253234 A1* | 10/2012 | Yang .................... A61B 5/1038 600/595 |
| 2015/0177080 A1 | 6/2015 | Esposito et al. |
| 2015/0254956 A1 | 9/2015 | Shen et al. |
| 2016/0206242 A1* | 7/2016 | Esposito ............. A61B 5/1038 |
| 2018/0018864 A1 | 1/2018 | Baker |

\* cited by examiner

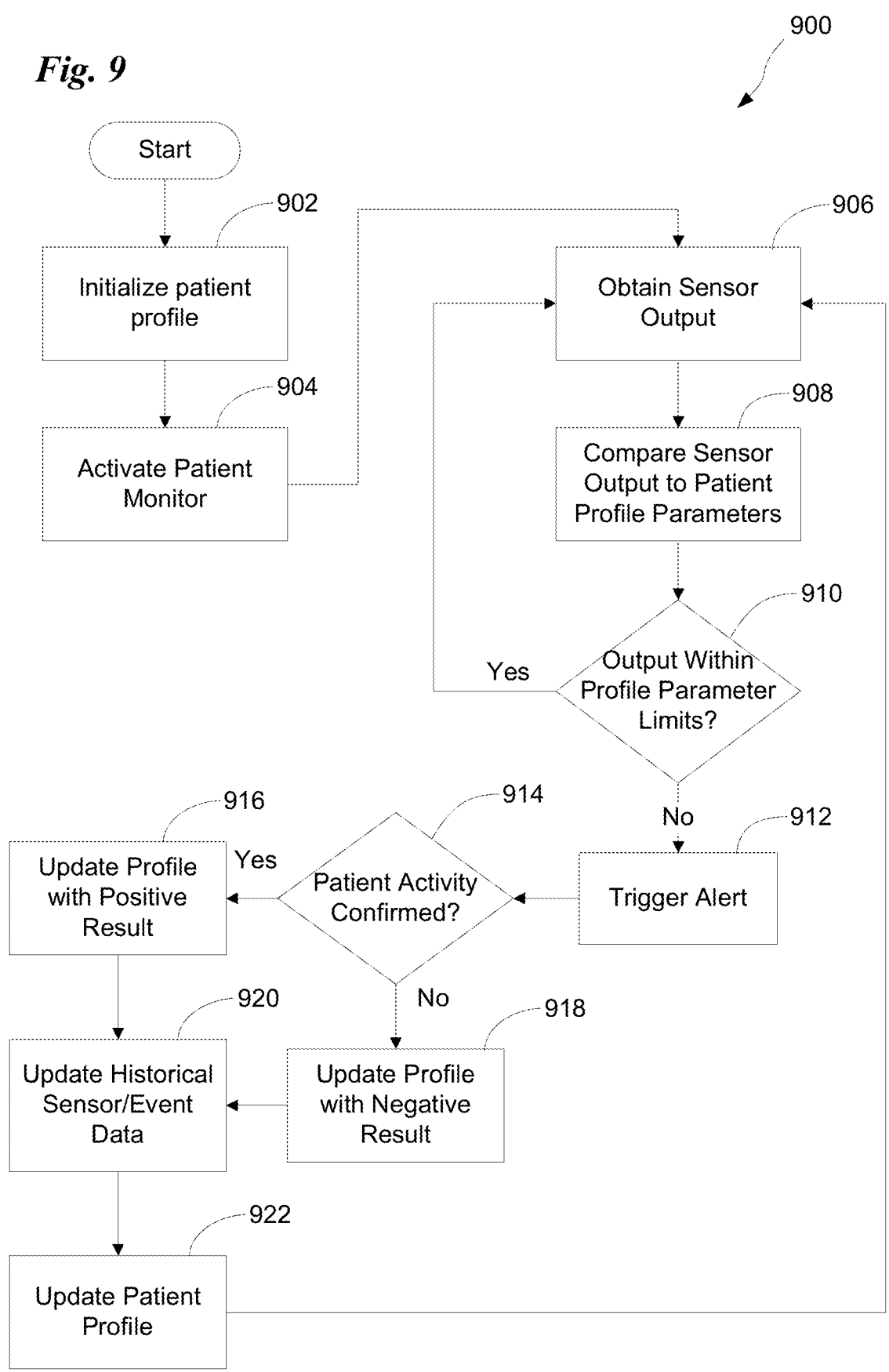

MOUNT FOR A PATIENT MONITORING DEVICE

CROSS REFERENCE TO RELATED APPLICATIONS

This application is a continuation of U.S. patent application Ser. No. 15/922,971 filed Mar. 16, 2018, which is hereby incorporated by reference.

BACKGROUND

The risk of a patient falling from a bed, chair, or other supporting structure is an important concern for those responsible for providing patient care. While patient falls are not always serious, the possibility of additional injuries to the patient, and the potential liabilities for caregivers makes avoiding patient falls an important concern.

Patients who fall may experience considerable pain and discomfort and may require additional time to heel old injuries that have been aggravated by the fall, or new injuries caused by the event itself. For healthcare providers, patient falls generally mean additional costs, some or all of which the facility may be forced to write-off. For insurance companies, the additional risk of injury from patient falls increases costs making it generally more expensive to provide health coverage to patients and liability insurance for hospitals and caregivers.

In some cases, monitoring equipment may be used to aid caregivers in determining when a patient may soon fall. Such equipment may interact with sensors in the patient's room, or mounted on the patient's body. Mounting devices for this equipment can be helpful for maintaining a secure and reliable connection between the monitoring device and the sensors, preferably without requiring specialized clothing that may be uncomfortable or easily damaged by the patient's normal movements. Preferably, such monitoring and mounting equipment is comfortable to wear and unobtrusive for the patient.

Thus patients, caregivers, and medical institutions would benefit from monitoring systems that can predict when a patient is about to fall that are easily installed and maintained.

SUMMARY

This disclosure generally relates to a mount for a monitoring device that can monitor patient activity in a hospital, clinic, nursing home, or other facility where a patient may be receiving care. More specifically, the disclosed mount can maintain a patient monitoring device on a piece of clothing worn by patient such as a sock that has pressure sensors in the sock itself.

In one aspect, the sock includes fibers in the fabric that are responsive to changes in pressure such as pressure occurring from a patient standing or walking. For example, the stress measuring fibers may include piezoresistive materials or properties. These stress measuring fibers change resistance as pressure is applied. To detect the changes in resistance, other conductive fibers are included in the sock fabric that carry changes in the resistance of the stress measuring fibers to a central location on the sock, such as just above the ankle. These changes in resistance may then be received and analyzed by a patient monitoring device.

In order for the monitoring device to receive the signals sent by the pressure sensing fibers, the patient monitoring device must be held in proper position and alignment in relation to the conductive threads. Proper alignment allows the proper terminals in the monitoring device to be electrically connected to the correct corresponding conductive fibers in the sock while still allowing the sock fabric to stretch or move somewhat for patient comfort.

As disclosed herein, a base portion may be used to clamp a portion of the sock fabric between a pad inside the sock, and a frame outside the sock. The pad may include one or more pins extending through the sock fabric and into at least a portion of the frame. The frame may include a mount portion and one or more terminals such that at least one of the pins is electrically connected to at least one of the conductive threads of the sock. For example, the pins may be positioned so that each pin passes through one or more of the conductive traces and into the frame.

Properly mounted, the patient monitoring device detects patient activity and reports this data in real time to a patient monitoring system. This system uses the reported information to predict when a patient is likely to stand, which may lead to a fall, for example, from a bed, chair, or other supporting structure. When the system determines that a fall is imminent, nearby caregivers may be alerted and can then offer timely assistance thus increasing the chance of avoiding a fall before it happens.

The patient monitoring device disclosed includes a monitoring device with one or more sensors such as a pressure sensor, accelerometer, gyroscope, temperature, proximity, or sensor that may be positioned on or near a patient. The monitoring device may receive updated sensor readings and can report this information to a central server. The server may then alert caregivers who are close by informing them that the patient's activities indicate a risk of an imminent fall.

The system may make this determination by comparing sensor readings with predetermined limits set for each particular patient. In one example, a pressure sensor may be incorporated into a patient's socks. The pressure sensor may include conductive threads woven into the fabric of the sock. When the threads are stretched or compressed the resistance of the circuit may change in response and may be detected by a monitoring device. In one example, the pressure sensor is the "Smart Sock" made by TexiSense of Montceau Les Mines, France. Excessive pressure, rapid changes in pressure, or other sensor readings may signal patient movement that may be potentially harmful.

The patient monitoring device may include a transmitter configured to send sensor information and/or alarm notifications to the remote server. When an alarm condition is detected by the monitoring device, an alarm message may be sent to the server which may automatically locate one or more caregivers closest to the patient. The alarm message may be sent to these caregivers indicating that an unexpected and possibly detrimental situation has occurred, or is about to occur, prompting caregivers to move to the patient to provide assistance.

Further forms, objects, features, aspects, benefits, advantages, and examples of the present disclosure will become apparent from a detailed description and drawings provided herewith.

BRIEF DESCRIPTION OF THE DRAWINGS

FIG. 9 is a flow chart illustrating actions that may be performed when triggering alerts in a patient monitoring system like the system of FIG. 1

DETAILED DESCRIPTION

Figure 1:
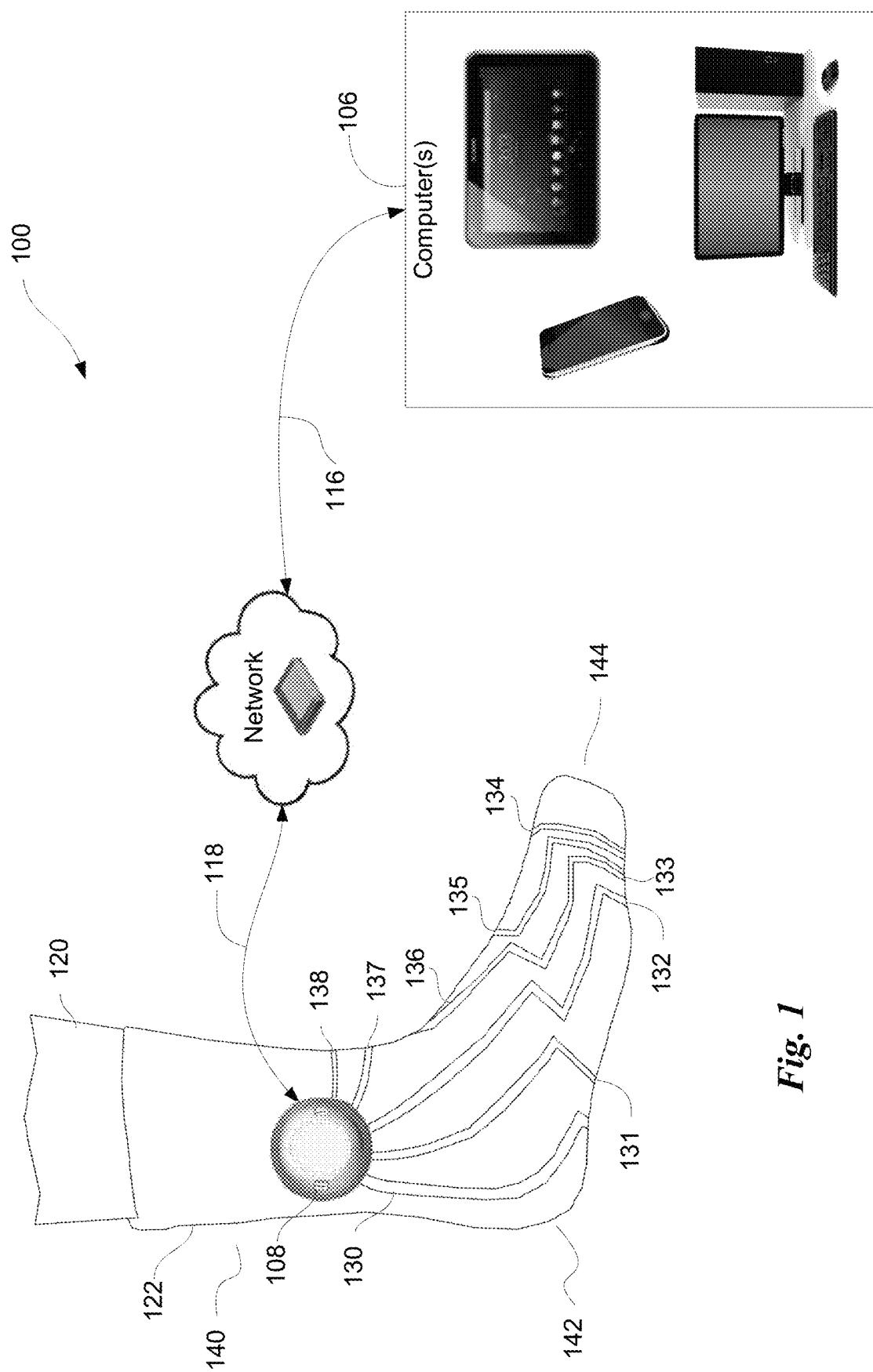
FIG. 1 is a component diagram illustrating exemplary components of a patient monitoring system as disclosed herein.

Illustrated in FIG. 1 is one example of components that may be included in a patient monitoring system 100. In this example, a monitoring system 100 includes a patient monitoring device 108 for detecting movements, combinations of movements, positional changes, and other patient activities or events that may indicate a patient is standing up, moving around, or about to fall. Monitoring device 108 may be coupled to a patient 120, for example, in a belt, an ankle bracelet, an armband, or as part of article of clothing such as a sock 122, shirt, gown, and the like. As shown in FIG. 1, monitoring device 108 is mounted to a sock worn on a patient's foot which may be configured to cover one or more of an ankle region 140, a heel region 142, and a toe region 144, or any combination thereof In other examples, the monitoring device may be mounted to other articles of clothing on other locations of a patient's body such as on a sleeve adjacent an arm or on a belt at the waist instead of, or in addition to, being worn in the ankle region.

Patient monitoring device 108 may communicate information with servers, databases, and/or other computers such as computers 106. These communications may be carried from monitoring device 108 to other devices using a communications links like communications links 116, and 118 that may also use a network 110. In one example, a computer 106 may be configured to discover what patient monitoring devices 108 are nearby using network 110, and may be configured to allow a caregiver using a computer 106 to select from which patient monitoring devices to monitor and receive alarm information.

Multiple circuits 130-138 may be included in sock 122 and electrically connected to terminals or contacts on monitoring device 108. Monitoring device 108 is held firmly in place relative to the circuits in the sock so that specific circuits 130-138 may be electrically connected to corresponding terminals of the monitoring device. Circuits 130-138 may also be electrically connected to one or more sensors included in the sock that are configured to detect activities of the patient thus providing signals representing output from the sensors to the monitoring device 108. Circuits 130-138 may, for example, include or be defined by one or more conductive threads woven into a portion of the fabric of the sock. In other examples, the circuits 130-138 may be attached to the fabric by weaving threads of the sock fabric through metallic traces, by adhering metallic traces to the sock fabric, or by any other suitable method.

Figure 2:
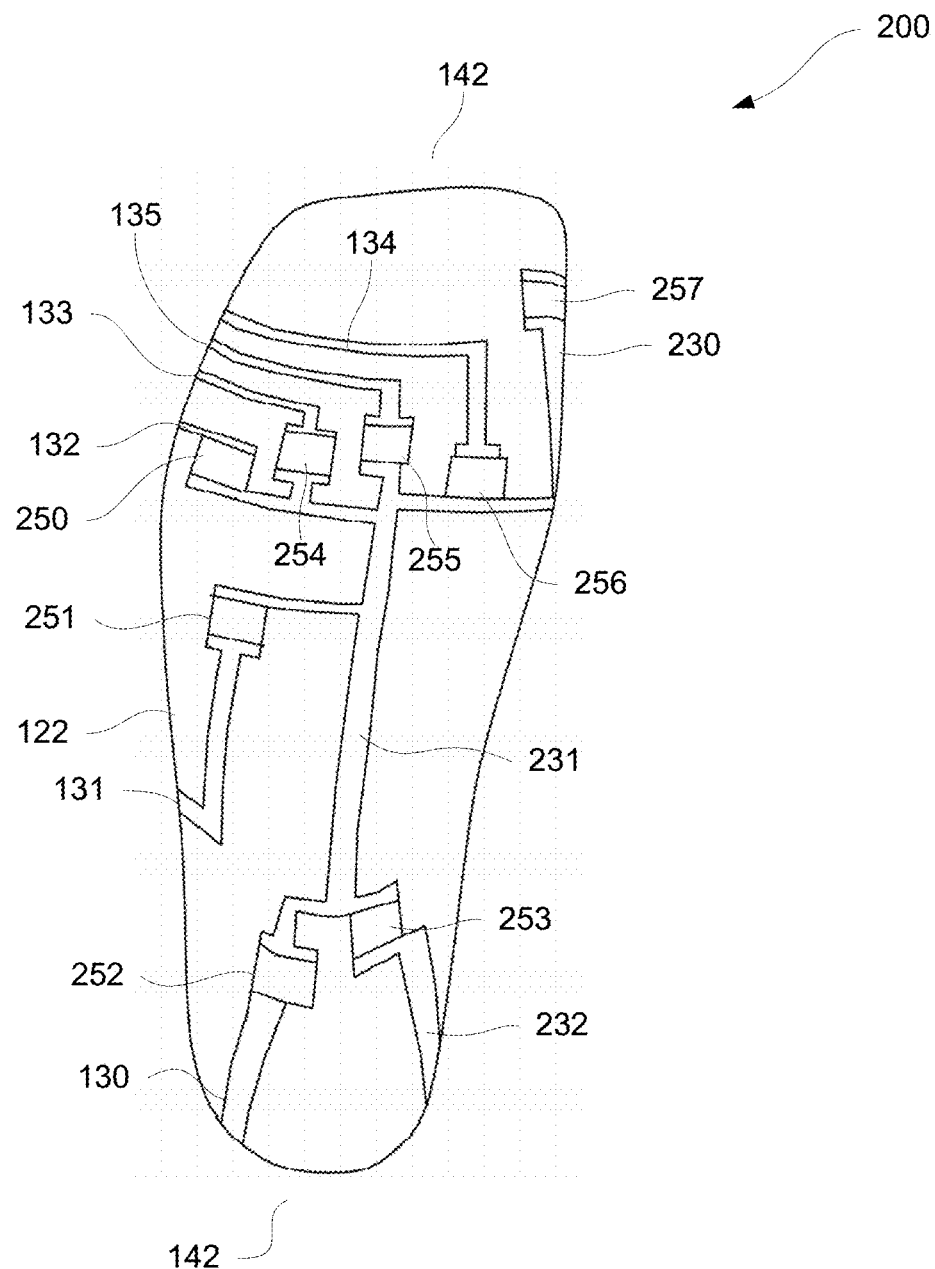
FIG. 2 is a schematic diagram illustrating pressure sensors on the sock of FIG. 1.

An example of one or more sensors electrically connected to circuits 130-138 is illustrated in FIG. 2 at 200. Pressure sensors 250-257 are positioned on the sole or bottom of the sock 122. Any suitable positioning arrangement of sensors is envisioned. For example, sensors 250, 254, 255, and 256 are arranged and configured to detect changes in pressure toward the front of the foot on the padded portion of the sole between the toes and the arch, sometimes referred to colloquially as "the ball of the foot". Put another way, sensors 250, 254, 255, and 256 are included in sock 122 at a location corresponding approximately with the forward or anterior portion of the metatarsal bones of the foot. This may be advantageous because pressures may tend to be be highest in this region of the foot. Pressures may vary laterally across this region meaning that pressures at the location of sensors 254 and 255 and may be somewhat lower than in the areas of sensors 250, and 256. Such a positioning of sensors can be advantageous because when standing, overall pressure on this region of the foot corresponds with supporting a significant portion of the weight a patient can place on the foot. Thus sensors 250, 254, 255, and 256 detecting changes in pressures in this location which can be helpful in determining that a patient may be moving to a standing position.

In another example also illustrated in FIG. 2, sensors 252 and 253 are positioned toward the rear of the foot corresponding with a location on the sole adjacent to the heel 142. In this example sensor 252 may be positioned to detect pressure on the lateral hind foot region of the foot, while sensor 253 may be positioned to detect changes in pressure on the medial hind foot region of the foot. These regions correspond approximately with the talus and calcaneus bones of the foot. Positioning sensors in these general areas can be advantageous because as with the "ball of the foot", overall pressure sensed at these locations correspond to supporting a significant portion of the weight placed on the foot by the patient. In some examples, about half of the patient's weight may be supported by the ball of the foot while most if not all of the remaining weight may be supported by the heel.

Other sensors may also be positioned on the sole of sock 122 which may be advantageous to further clarify whether a patient is moving to a standing position, walking, carrying excessive weight, and the like. For example, sensor 251 may be placed adjacent the midfoot region approximately corresponding with the cuneiform bones of the foot. In another example, sensor 253 may be placed on the sole of sock 122 to correspond with and measure pressure on the "big toe" or hallux of the foot. Any suitable arrangement of pressure sensors may be included to register pressures on other regions such as the individual toes, and the like.

The sensors shown in FIG. 2 may be of any suitable type or construction. For example, sensors 250-257 may include piezoresistive fibers, which is to say, fibers which change resistance as the pressure exerted on them changes. In one preferred embodiment, these resistive fibers may be woven together with the threads of the fabric in the general area of locations 250-257. Thus sensors 250-257 may alternatively be thought of as regions of the garment fabric with increased sensitivity to changes in pressure resulting from the addition of resistive fibers. In other examples, a pressure sensor maybe be inserted into the garment at 250-257 such as by removing a portion of the fabric and replacing it with a sensor unit, or with other fabric that includes the resistive fibers. A pressure sensor may also be inserted into the fabric and maintained between the inside and outside surfaces. In another example, the pressure sensors may be attached to the fabric such as by an adhesive or by other means. Thus pressure sensors may be included with the fabric by any suitable technique, but preferably without substantially increasing the thickness of the garment fabric, and/or without adding heavy or bulky devices that are unpleasant for the patient. Preferably, the sensors are mounted in a way that in an unobtrusive and comfortable.

Thus monitoring unit 303 may measure these changes in resistance and determine the pressure at each sensor location accordingly. However, any suitable pressure sensing technology may be used. As illustrated in FIGS. 1 and 2, circuits 130-138 are arranged to provide sensory input from sensors 250-257. Additional circuits may be included in the sole portion of sock 122 to facilitate the transfer of input to monitoring unit 108. For example circuits 230, 231, and 232 may be included in electrically connected to circuits 130-138. Any suitable arrangement of circuitry may be used including those illustrated in FIGS. 1 and 2.

Figure 3:
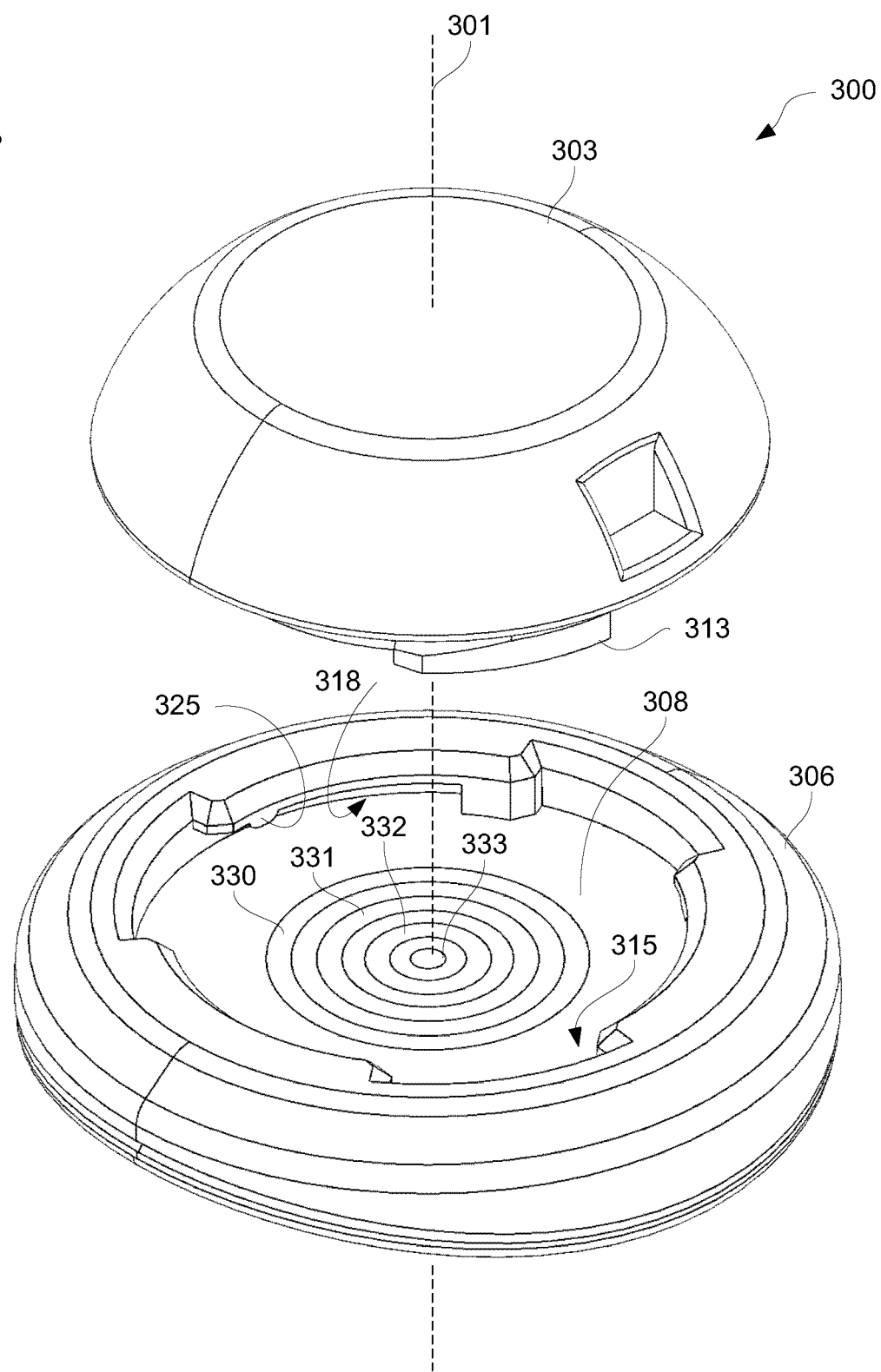
FIG. 3 is a perspective view of major components of the patient monitoring device of FIG. 1.
Figure 4:
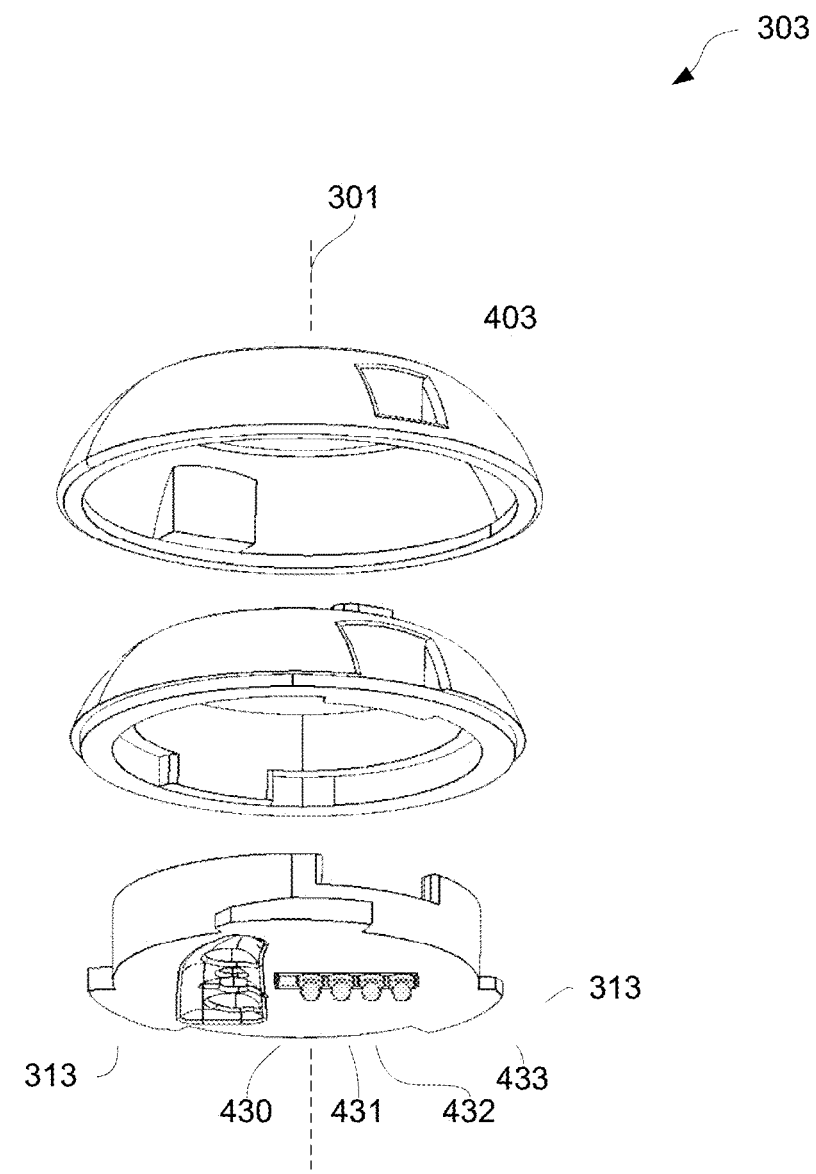
FIG. 4 is an exploded view of a monitor portion of the device in FIG. 3.
Figure 5:
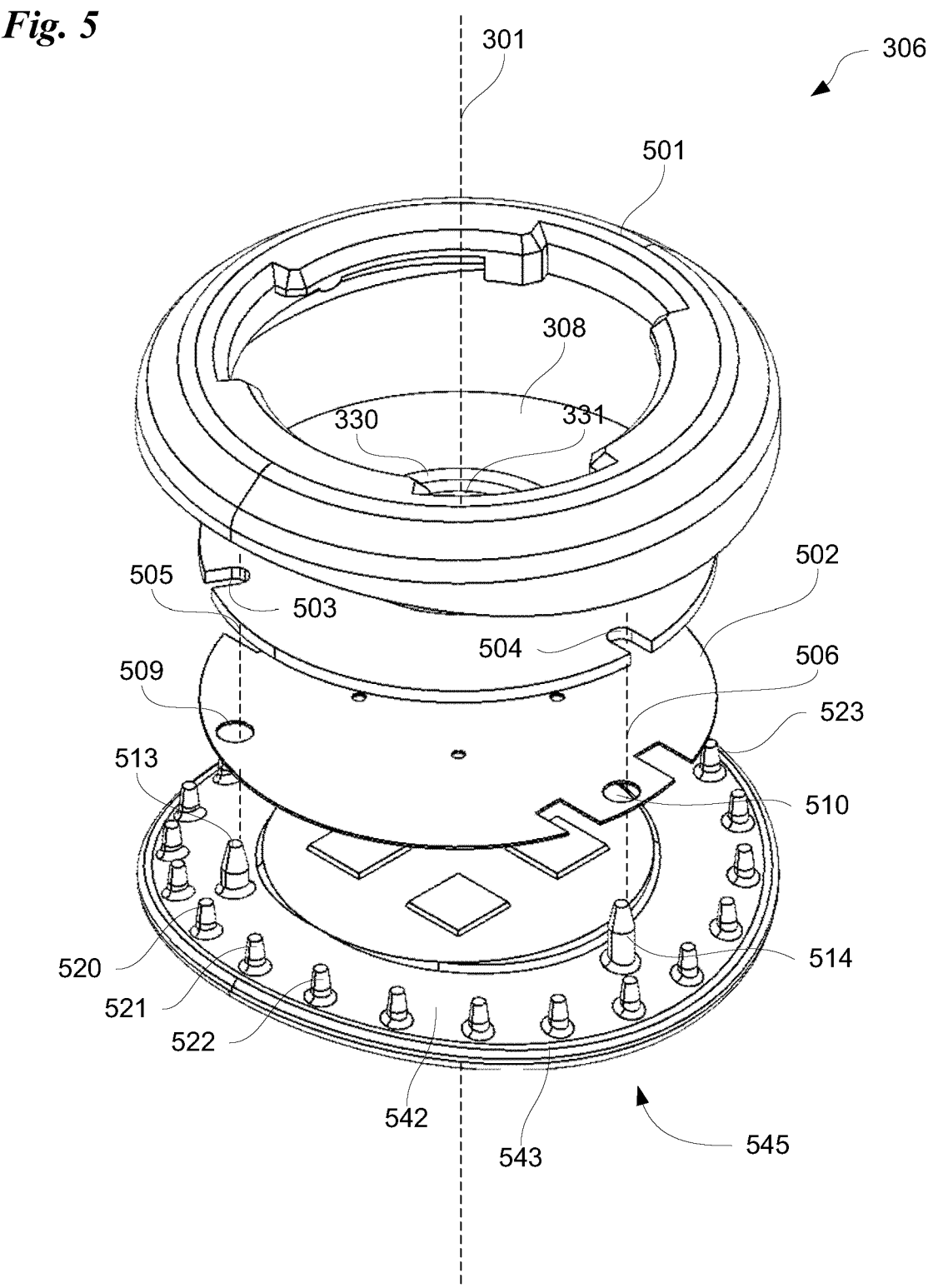
FIG. 5 is an exploded view of a base portion of the device in FIG. 4.

FIGS. 3-5 illustrate aspects of a monitoring device like monitoring device 108 that may be positioned on a sock or other garment to detect and respond to changes in patient activity. In FIG. 3, a monitoring device 300 has a patient monitor 303 that can be held in place on the garment by a base 306 which may also be referred to as a mounting unit or dock. Base 306 can be coupled to the garment allowing monitor 303 to be maintained on the garment by then mounting the monitor 303 to the base 306. This mounting may be achieved in any suitable manner including any arrangement of retention members on the monitor and base. In one example, monitor 303 may be oriented by rotating on an axis 301 so that flanges or ribs 313 extending out away from monitor 303 can pass through openings like opening 315 defined by the base. This allows a lower or inner portion of monitor 303 to be inserted into an open area defined by base 306. Monitor 303 may then be rotated around axis 301 in a clockwise direction to allow flanges 313 to be retained in place within channels 318 also defined by the base. In this way, monitor 303 is mounted to base 306 and can be selectively transitioned from a first unmounted position to a second mounted position on or in base 306. Flanges 313 may include locking members, such as a raised portion or ridge 325 that extends toward a flange 313 to lock the flanges in place when the monitor is rotated into position. In another example, flanges 313 may be replaced by or include threads engaging corresponding threads in the base. Monitor 303 may be retained to base 306 by any suitable method such as by fasteners inserted into the monitor and base, clips, clamps, snaps, and the like.

Monitor 303 and base 306 may be electrically connected together by any suitable wired or wireless communication. For example, one or more conductive wires or traces may be included in a circuit board 308 as part of base 306 and configured to electrically connect with corresponding terminals in the monitor unit 303. One example of one or more such corresponding terminals is illustrated in FIG. 4 as terminals 430-433. Terminals 430-433 extend toward base 306 from a frame 411. The conductive traces may be arranged as shown in FIG. 3 where traces 330-333 are positioned on circuit board 308 in a predetermined pattern shown here as multiple circular traces extending outwardly from a central location on the base unit. In this example, traces 330-333 are centered on circuit board 308 in a location corresponding to axis 301 thus allowing pins of multiple terminals extending from the monitor 303 toward the base 306 to individually electrically connect to the traces. When monitor 303 is inserted and rotated into a locked position, the terminals remain in contact with the traces regardless of the angular position or rotation orientation of the monitor with respect to the base. Thus multiple circuits within the monitor 303 can separately connect electrically with multiple circuits in the base 306 while allowing the monitor to be selectively separable from the base.

Other aspects of monitor 303 appear in FIG. 4. A cover 407 may be included and positioned over frame 411 to coincide with central axis 301. Cover 407 may be coupled to frame 411 by any suitable means such as by fasteners such as clips, screws, or pins, or by glue or other adhesives. Additionally, an over-mold 403 may be optionally included and positioned over cover 407.

One example of components that may be included in base 306 appears in FIG. 5. A chassis 501 may be included that can be coupled to a pad 545. Between the chassis and the pad, a circuit board 308 may be aligned with other components of the base on axis 301. Circuit board 308 may also define alignment holes or slots 503 and 504 which may be included at locations on circuit board 308 and indexed by alignment pins 513 and 514 in pad 545. Alignment pins 513 and 514 thus define alignment axes 505 and 506 respectively providing points of reference for components of base 306 to be properly positioned with respect to one another.

A protective cover 502 may be included to protect the fabric that base 306 is mounted to from being damaged by electrical contacts or components mounted to circuit board 308. In another aspect, the protective cover 502 may be useful for protecting the circuit board 308. For example, cover 502 may be formed of or include an electrically insulative material to reduce or eliminate electrical exchange between the fabric of a sock or other garment and the circuitry in circuit board 308. Protective cover 502 may define holes or slots 509 and 510 which also may align with alignment pins 513 and 514 along alignment axes 505 and 506.

Pins 513 and 514 may also be configured to retain pad 545 adjacent chassis 501 thus allowing chassis 501 to be selectively separated from pad 545. For example, pins 513 and 514 may engage retention members in chassis 501 to firmly clamp fabric between the pad and chassis. Such retention members in the chassis may be clips, friction fittings, or threaded receptacles in the case where pins 513 and 514 include threads and can be rotated to tighten the pins into the receptacles. When separated, chassis 501 may include circuit board 308 and protective sheath 503 while the remaining components may be separated together as part of pad 545.

Pad 545 may also include a pin array including one or more pins or studs, examples of which include pins 520-523. The pins in the array may extend outwardly from a pin mount 542 of pad 545 towards chassis 501 and may engage the chassis at one or more corresponding holes, slots, or channels defined by the chassis 501. These channels may include conductive terminals allowing an electrical connection to be made between the pins and interior portions of chassis 501.

Figure 6:
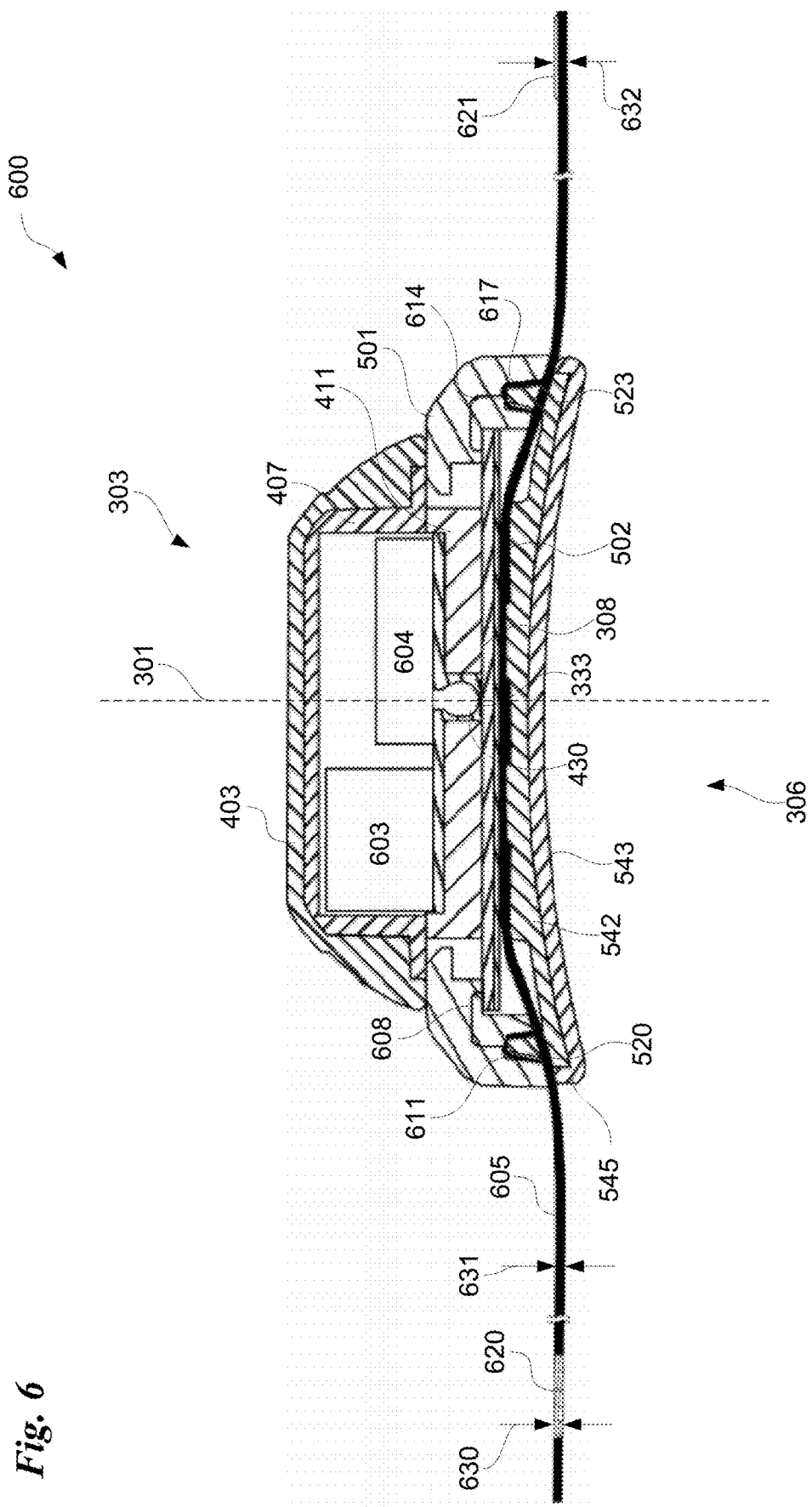
FIG. 6 is a cross sectional view of the patient monitoring device of FIGS. 1-5 mounted on fabric.

FIG. 6 illustrates at 600 a cross sectional view of one example of a monitoring unit mounted on a garment such as a sock. The monitoring unit 303 includes a battery 603 for providing power to a control module 604. Control module 604 may include additional sensors, processing logic, and the like, for detecting patient activities and alerting caregivers. Additional circuitry or electronics may be included as well, which is discussed in further detail below.

Fabric 605 may include one or more sensors such as pressure sensors discussed above with respect to FIG. 2. A concentration of piezo resistive threads woven into fabric 625 operating as a pressure sensor is shown at 620. In this example, the sensor has a thickness illustrated at 630, that is less than or equal to the thickness of fabric 605 shown at 631. This type of low-profile arrangement is advantageous because the sensor is less noticeable to the user and more comfortable. In another example, a pressure sensor 621 is mounted to an outside surface of fabric 605. This example is less preferable because the thickness of sensor 621 shown at 632 is greater than the thickness of the fabric. Such an arrangement can be used successfully, but is less advantageous because it is more noticeable to the person wearing the garment. Regardless of construction, sensor input from sensors in fabric 605 (like 620 and 621) may be relayed to control module 604 for processing by any suitable means such as by conductive threads woven into fabric 605, by traces fastened to the fabric, or by other means as discussed above.

Positioning fabric 605 of the sock between protective sheath 503 and pad 545 thus clamps the fabric between the pad and the chassis 501 of the base 306. For example, a caregiver may reach inside the garment and position the pad 545 in the proper place aligning pins 520 and 523 so that they pass through fabric 605 in the proper locations to electrically connect to traces or other conductive circuitry included in garment. The caregive presses the pad against the fabric so that pins on the pad such as pins 520 and 523 pass through fabric 605. The caregiver then arranges the chassis 501 on the outside of the garment and orients it to align the pins with openings defined by chassis 501 before securing the pad and chassis together with the garment fabric between.

Circuits in the fabric 605 may then carry electrical signals from the circuitry, through the fabric, and into the monitoring unit 303. This communication is facilitated by conductive terminals 611 and 617 which may be electrically connected to circuit board 308. Traces on (or in) circuit board 308 carry the signals to traces 333 which is are in contact with terminal 430 of the monitoring unit 303. Thus control module 604 is electrically connected to the sensors in the fabric 605. This configuration minimizes or eliminates movement of fabric 605 relative to the base 306 allowing conductive leads or traces in fabric 605 to be maintained in the proper position relative to pins in the pad without the need for studs or pins to be mounted in fabric 605 directly.

Figure 7:
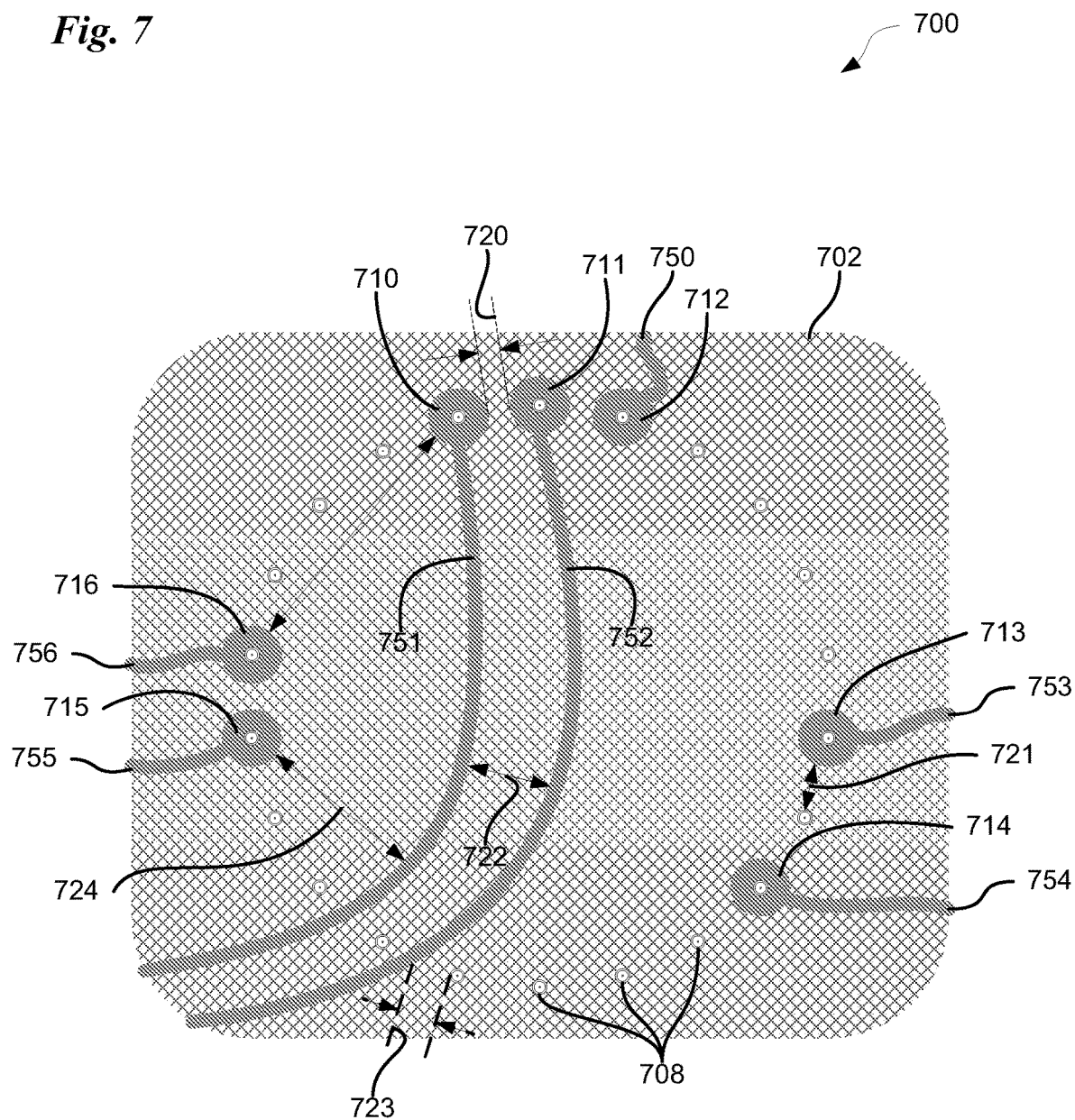
FIG. 7 is a schematic diagram illustrating aspects of the spatial relationship between the mount of FIG. 1, and the mounting garment.

An example of this is further illustrated in FIG. 7 at 700 where fabric 702 is shown with multiple pins 708 penetrating through the fabric as discussed above with respect to FIG. 6. FIG. 7 illustrates how a pad like pad 545 in FIG. 6 might appear as the patient monitoring unit is installed on a patient garment. As noted above, the pad is placed behind or inside the garment and pressed into place so that pins 708 pass through the fabric of the garment. The caregiver positions the pins 708 in accordance with the conductive circuits 750-756 which may be woven into or otherwise included in the fabric. This allows the unit toelectrically connect to sensor elements also included in the fabric as discussed above. Fabric 702 optionally includes contact regions 710-716 which are electrically connected to circuits 750-756 with each circuit terminating in a separate contact region as shown (e.g. patch 710 is connected to circuit 751, patch 716 to circuit 756, and so forth). This arrangement may be included to aid in positioning pins 708 to electrically connect to circuits 750-756 allowing circuits 750-756 to be smaller or narrower possibly reducing cost and/or perhaps increasing aesthetic appeal. In another aspect, regions 710-716 may define holes through which pins 708 can pass to aid in proper alignment and electrical conductivity. In those cases where the fabric 702 does not include contact regions associated with circuits 710-716, the circuits themselves may include such holes.

Once the pad is inserted through the fabric with the proper pin alignment, and the chassis portion of the base unit is secured in place over the pins, the fabric 702 is secured in place by the penetration of the pins, and by the friction created by the clamping action of the pad and chassis on opposite sides of the fabric. The compressions forces between the pad and chassis are created at least in part because the surfaces in contact with the fabric are substantially planar. Stretching and displacement of fabric 702 held between the pad and chassis and adjacent the pins 708 is thus minimized or eliminated. This allows dimensions such as at 720 between two contact patches 710 and 711, or dimension 722 between two circuits 751 and 752 to be carefully maintained to reduce or eliminate the opportunity for short circuits. The clamping action of the base and pad also reduces stress on the fabric at the points where the pins 708 pass through. Maintaining the fabric in the proper position reduces or eliminates changes to other dimensional aspects such as the distance between a contact patch and a circuit at 724, the distance between a contact patch and an adjacent pin at 721, and the distance between a circuit and a pin at 723 to name a few non-limiting examples.

Thus positioning of conductive traces or circuits in fabric 702 may be arranged in a specific predetermined pattern which may involve close spatial tolerances without the added complexity of mounting pins into the fabric 702 itself. As illustrated herein, the conductive pins 708 are mounted to a pad behind the fabric and configured to pass through from one side to the other. Production as well as care and maintenance of the fabric are thus reduced without the added stress points introduced by mounting pins in the fabric itself.

The pattern of circuits and patches illustrated in FIG. 7 follows a substantially circular ring, but any suitable pattern may be used (e.g. a single row of pins, rows of pins at right angles such as in a "cross," a rectangle arrangement, rows of pins in a grid pattern, rows of pins following a curved path such as an arc, and the like). Other patterns may require a different arrangement of traces or circuits in the fabric, and possibly a different chassis with a corresponding shape, or with corresponding arrangements of channels, slots, or holes to accommodate the pins.

Figure 8:
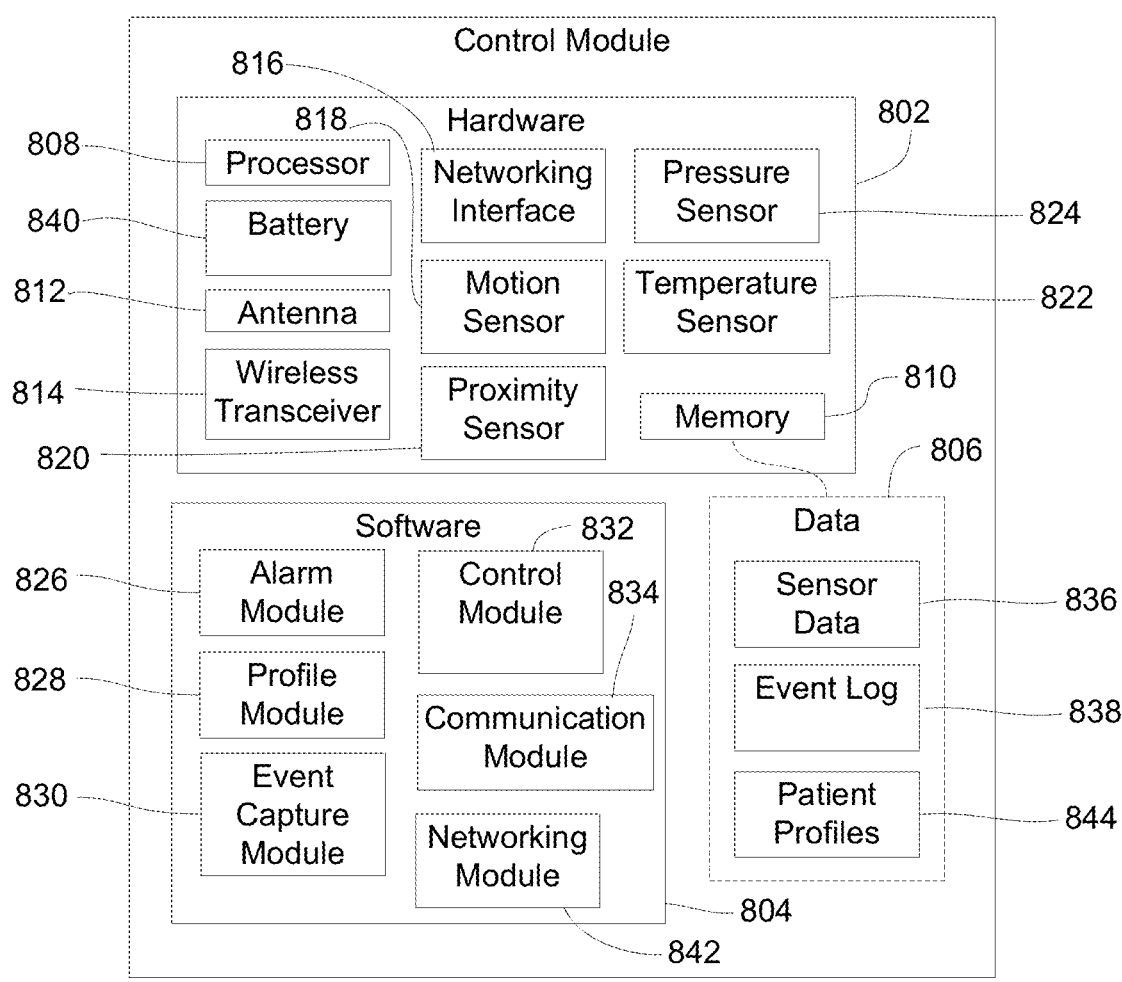
FIG. 8 is a component diagram illustrating aspects of a patient monitoring device like the is patient monitoring device in FIG. 1

Additional detail of the software, hardware, and data aspects of a system like the one illustrated in FIG. 1 is further illustrated in FIG. 8. As noted in FIG. 6, the monitor may include any suitable electronic components for monitoring patient activity. Such components may include a battery 603 and a control module 605. FIG. 8 illustrates at 800 one example of hardware and software that may be included in a control module like control module 605. A control module may generally include hardware 802, software 804, and may optionally include a local data store 806. Any suitable arrangement of hardware or software modules may be used.

Hardware 802 may include a processor 808 which may be programmed to perform various tasks discussed herein related to monitoring patient activity. Processor 808 may be coupled to other aspects of hardware 802 such as sensors, memory, and the like to perform these tasks. Memory 802 may be included for storing operating values or parameters which may include intermediate or final values of calculations, logical or computational instructions for processor 808, or hardware control parameters. Memory 802 may also store patient monitoring information such as patient related events in an event log 838, sensor data 836 obtained from sensors coupled to the patient monitoring device, and/or patient profiles 844 for controlling how data about patient activity is collected and analyzed. Memory 802 may be either a permanent or "static" memory, or a temporary or "dynamic" memory, or any combination thereof.

An antenna 812 may be included to facilitate wireless communications over a communication link like communication link 118. A networking interface 816 may be included to process communications with other devices in the system communicated using a network such as network 110. Wireless transceiver 814 may be included and may use antenna 812 or other suitable hardware 802 to transmit and receive information between control module 800 and other devices in the patient monitoring system such as servers, data stores, and/or computers like computers 106.

Control module 800 may include one or more sensors such as a motion sensor 818 configured to detect a patient's movements. Motion sensor 818 may be any suitable device or devices responsive to the movement of the patient and may include, for example, one or more accelerometers to detect movement in multiple axes relative to gravity, and/or one or more gyroscopic sensors for detecting changes in angular momentum and/or an angle of elevation. Motion sensor 818 may be used to detect when a patient changes position to get out of bed, or abruptly falls to the floor from a standing position, or from a supporting structure such as a bed, chair, wheelchair, and the like.

Hardware 802 may also include proximity sensor 820 configured to generate signals based on distance from a target object or location. For example, a sensor target object such as a magnet, a radio transmitter, or other target may be positioned in or adjacent to a chair or bed, or other reference point. Proximity sensor 820 may determine the distance between sensor 820 and the sensor target and provide this information as a time varying signal to other software or hardware components of control module 800. For example, this proximity data may be processed by processor 808 according to software 804 and used to determine when a patient has traveled beyond a predetermined threshold distance from the sensor target as defined in the patient's profile.

A pressure sensor 824 may also be included, and may be useful for detecting changes in the distribution of pressure on a patient's body. For example, pressure sensor 824 may detect an increase in pressure in one body part, and a decrease in pressure in another as a patient moves from laying down to being seated upright. Pressure sensor 824 may also detect rapid drop in pressure on a particular body part when a patient is falling, and a subsequent rapid increase in pressure when the patient lands abruptly on a support surface such as the floor or the ground.

The temperature sensor 822 may also be included to provide further information about patient's location, position, and/or overall health. For example temperature sensor may be useful for determining when a patient removes the sensor from their body, when a patient moves outside a facility, or enters an environment that causes a large change in the patient's temperature, or in the temperature of the environment.

Any of the sensors used by control module 800 such as sensors 818, 820, 824, 822, and others, may be mounted inside or outside a housing containing some or all of the other hardware and software components. For example, patient monitoring sensors may be mounted outside a container or housing and may communicate with hardware and software inside the housing by any suitable communications link. For example, pressure sensor 824 may be woven into a patient's clothing such as into a sock or gown, and may communicate with components of software 806 and hardware 802 mounted inside the housing via a wired or wireless communications link. This communications link may be maintained as electromagnetic signals traveling over wire leads, or through the air as radio waves using any suitable wireless communication technology.

These hardware aspects of control module 800 may be configured to operate according to instructions included in software 804. These instructions may be logically or conceptually arranged as modules for controlling different functional aspects of the patient monitoring device. Functional aspects generally include obtaining, storing, and processing data from multiple sensors, detecting patient activity, determining when to send alert notices to other parts of the system, retrieving or updating patient profile information, and/or sending sensor data to a central archive to improve the performance of patient monitoring devices throughout the system.

Software 804 may include an alarm module 826 configured to send alarm related messages, events, or data to other parts of patient monitoring system 100. Alarm module 826 may determine when to send alert information notifying caregivers when a change in a patient's situation warrants immediate investigation. Alarm module 826 may include rules for determining under what circumstances an alert should be sent. In one example, alarm module 826 uses a patient profile 844 that has one or more patient related parameters with corresponding predetermined threshold values. These values may be used to determine when patient activity warrants further investigation.

Examples of alarm rules include a pressure rule that is triggered when signals are received from alarm module 826 that indicate changes in position or other activity that may have caused pressure differentials in the patient's feet or other monitored locations that are outside the predetermined threshold values in a patient profile 844. Such pressure sensor rules, when triggered, configure control module 800 to send an alert indicating that changes in the pressure distribution of a patient's weight relative to a support surface no longer match the predetermined patient profile. In one example, the patient has been prescribed bed rest resulting in a predetermined target distribution of weight across the patient's back and legs stored in patient profile. This weight distribution may be periodically or continuously detected by pressure sensor 824 as signals sent from the pressure sensor to other parts of patient monitoring device for processing and storage. When a patient moves, such as to an upright seated position, pressure sensor 824 may begin sending different signals indicating a different distribution of weight that no longer matches the patient's profile. A rule in alarm module 826 may then be triggered to send data, message, an event, or any other suitable series of instructions or data to other parts of the patient monitoring system indicating that the patient has changed position.

In another example, alarm module 826 may include motion rules that may be triggered when motion sensor 818 indicates movement that falls outside the predetermined threshold values in patient profile 844 that are related to motion. Such motion related parameters in the patient profile 844 may include any combination of movement in general areas such as the patient's extremities, torso, or in specific areas such as movement of the head and neck, movement of an arm and/or leg, and the like. Such movement may include changes in the speed, acceleration, or angle of incidence relative to gravity for a give part of the patient's body. Patient profile 844 may be stored in memory 810 along with other relevant data and may be used to maintain these parameters which may be generic to many patients, or specific to the particular patient wearing control module 800.

In another example, the alarm module 826 may include proximity rules that are triggered when a patient travels beyond a predetermined distance from a target location such as a bed, chair, or other supporting surface. For example, proximity sensor 820 may send signals continuously or at regular intervals to control module 800 indicating the range to the target object. When the patient moves, proximity sensor 820 may send different signals indicating a change in distance to the sensor target. The rule in alarm module 826 may be triggered to send information to other parts of the patient monitoring system in the event that proximity sensor 820 indicates a range from the sensor target that exceeds a predetermined threshold in the patient's profile 844.

In yet another example, alarm module 826 may include motion sensor rules that when triggered, configures control module 800 to send alerts when the patient's movements do not match the patient's profile. Using motion sensor 818, patient's movements may be periodically or continuously processed by control module 800 as signals from the motion sensor change over time. At some point, patient's movements may change causing motion sensor 818 to send signals indicating a movement or series of movements that no longer match the patient's profile. A motion sensor rule in alarm module 826 may then be triggered to send event data to other parts of the patient monitoring system indicating that the patient's movements suggest activity that is outside the patient's predetermined thresholds in the patient's profile and thus may be or detrimental to the patient.

Alarm module 826 may be programmed with any suitable series of rules comparing the current state of control module 800 to one or more predetermined threshold values. For example, alarm module 826 may include rules that are triggered based on combinations of input from multiple sensors received over time. These combinations may be defined in a monitoring rule, or in patient profile 844. In this way, one or more combinations of signals from one or more sensors may be considered over specific time intervals allowing for more complex considerations of data received from motion sensor 818, pressure sensor 824, temperature sensor 822, proximity sensor 820, and any other sensors that may be employed.

In another example, alarm module 826 may be configured with one or more status related rules. Such rules may include a wireless networking rule configured to trigger when wireless transceiver 814 reports signal strength from nearby wireless devices has fallen below a predetermined threshold. Another status rule may include a battery monitoring rule configured to trigger when the state of charge for a battery 840 is below a predetermined threshold. Others such status rules may include an error reporting rule configured to trigger when a hardware or software error condition occurs, when available storage capacity in memory 810 is below a predetermined threshold, and the like.

Alarm module 826 may also be programmed to include an alert level, severity level, level of importance, or other similar flag or indicator to assist the patient monitoring system in prioritizing, categorizing, or managing the response to alarms or alerts that may be raised. Alarm module 826 may include rules for calculating this priority level. For example, an alarm rule may be configured to set the severity level of an alarm to indicate a high degree of importance in the case where a particular threshold value (e.g. patient's movements) exceeds parameters set in the patient's profile by greater than a predetermined severity level threshold. Priority levels may be indicated in any suitable fashion such as a range of numbers zero through nine or zero through a hundred and the like, or a "high", "medium", and "low" indicator.

For example, if a patient's movements exceed parameters in the patient profile by less than 10%, alarm module 826 may generate an alarm with the severity level that is at a lower level such as zero or one or "low". When the patient's movements exceed the upper range of a patient's profile by for example 10-30%, a higher level may be assigned such as a three, or four or a "medium" indicator may be used. For situations where patient movement exceeds the patient's profile parameters by greater than 30%, a "high" indication may be assigned to the alert information, or a value such as eight or nine. This is but one non-limiting example as any suitable scheme for prioritizing alarm information may be used.

Profile module 828 may be configured to accept or modify or otherwise maintain a patient profile 844. Patient profile 844 may include multiple parameters detailing information about the patient, the patient's treatment plan, and other information useful to control module 800 and the rest of patient monitoring system 100. A patient profile may include any information about the patient useful for predicting and preventing patient falls. Such information may include detailed patient measurements such as medical condition, height, weight, body composition, treatment plans, drug regimens, and the like. It may also include demographic information such as sex, race, and the like.

For example, a patient profile may include parameters indicating whether a patient should be allowed to move away from a supporting surface such as a bed or chair, whether the patient should be allowed to assume a particular posture or position such as standing, walking, sitting, laying down (left and/or right side), and the like. A patient's profile may indicate under what circumstances a patient may leave the room, or how often the patient should be repositioned in place.

Parameters, or parameter ranges may be specified in any suitable format such as numbers, letters, binary data, and the like. For example parameters may be organized to correspond with input values required by one or more rules in alarm module 826. In another example, patient parameters may be configured to correspond with output ranges of specific sensors or combination of sensors used by control module 800. The patient parameters may be thought of as predetermined threshold values that may be compared to sensor or other data according to a rule. These predetermined threshold values may be specific values or ranges of values, with or without accompanying tolerances. Such values may be numerical, textual, or any combination thereof.

An event capture module 830 may be configured to collect available event related information to send out to other parts of patient monitoring system when an event occurs. This information may include a snapshot of the patient's present condition and state as determined by the sensors in control module 800. A current reading from the motion sensor 818, proximity sensor 820, pressure sensor 824, temperature sensor 822, and/or the state of various subsystems in control module 800 such as battery 840, memory 810, or any combination thereof. Event data may also include the rule triggered, date and time stamp, and the like.

Event capture module 830 may collect event information when alarm is triggered, or periodically to provide patient monitoring system 100 with an ongoing regular status update of the patient's condition, position, activity, and the like. Event capture module may include rules specific to general event capture irrespective of whether an alarm state has occurred. For example, an event capture rule may store event information in an event log 838 in memory 810 when patient activity occurs but is not outside the parameters specified for such activity in patient profile 844. This may be advantageous in providing "baseline" values for the state of a patient leading up to an alarm condition when it occurs. Event data may be stored in event log 838 and transferred to a remote data store.

Other contextual information may be collected as well and sent along with an alert or event update. Such contextual information may include signals or other data received from sensors or other parts of control module 800 for a predetermined time period prior to the alert being sent. For example the alarm module may collect all data obtained or received by control module 800 for the last 60 seconds before the alert was sent, for the last five minutes before the alert was sent, for the last half an hour, or for some period of time greater than a half an hour. In another example, the transmission of data may be based on a number of events rather than a specific period of time. This data may include all available monitoring data, or some portion of the data as determined by the triggered rule, or by alarm module itself to 826.

In one example, when a motion sensor rule is triggered, the rule may be configured to collect the preceding two minutes of motion sensor data and/or the preceding five minutes of pressure sensor data to be sent with the alarm message. In another example, alarm module 826 may be configured to collect the preceding five minutes of data from some sensors (e.g. pressure sensor, proximity sensor, and or motion sensor) but not others (e.g. temperature sensor). In another example, stored data from all sensors may be collected by 826 after a predetermined number of events have been detected and stored from a number of different sensors. This kind of "pre-alarm" data may be used by other parts of patient monitoring system to detect patterns of sensor data that indicate certain patient activity is imminent or to determine probabilities of false positives and false negatives. This information can be used to refine when rules should trigger.

Assembled data may be organized into an alarm message which may include the current snapshot of the patient's condition and any other information related to the alarm that may be useful to other parts of the patient monitoring system. The message may be transmitted over a communication link using networking interface 816 to be processed by a remote server, or seen by an operator at a computer such as computer 106. Alternatively or addtionally, the data may be stored in remote data store along with associated sensor data.

Control module 832 may be included to organize the operations of software 804 and/or hardware 802. Control module 832 may be configured to initialize the activity of control module 800 such as going through a basic startup and testing procedure, running through algorithms or subroutines to locate and communicate with remote servers or databases, or other computers like computer 106, and/or other devices in the patient monitoring system. Control module may then begin one or more control loops periodically or continuously obtaining sensor data from one or more sensors in the patient monitoring device such as pressure sensor 824, motion sensor 818, proximity sensor 820, and or temperature sensor 822 or others. Control module 832 may be thought of as a "controller" that controls the operation of patient control module 800.

A communication module 834 may be included as well. Communication module 834 may be configured to open and maintain communication links to various other parts of the patient monitoring system such remote servers or databases, and others. Communication module 834 may be configured to implement any suitable digital, analog, or other communication scheme using any suitable networking, or control protocol. Communication module 834 may engage or use networking module 842 to open, maintain and manage communication links with other aspects of the patient monitoring system via network.

In one example, communications module 834 may be configured to automatically establish communication link 118 with network 110. Patient control module 800 may be configured to operate according to the IEEE 802.15 wireless networking standard (sometimes referred to as a "Bluetooth" or Wireless Personal Area Network or "WPAN"). In this example, communications module 834 may automatically interact with routers, switches, network repeaters or network endpoints, and the like to establish a communications link 118, and/or 112 so that event updates may be automatically configured to pass to a remote server where they may be processed and distributed. Communications module 834 may be implemented to use any combination of Generic Access Profile (GAP), Generic Attribute Profile (GATT), and/or Internet Protocol Support Profile (IPSP) protocols to acquire and maintain communications with remote servers, databases or computers.

Control module 800 may maintain data 806 which may include sensor data 836, event log 838, and one or more patient profiles 844. Data 806 may include diagnostic information, timestamps and other contextual information related to actions taken by patient control module 800, alarm messages sent, raw sensor data, and the like. Data 806 may be accessed by other software or hardware in patient monitoring system 108. Data 806 may be periodically refreshed or deleted to optimize use of memory 810.

Stored patient profiles 844 may include default parameter values general to many patients, or parameter values specific to one patient. These parameter values may be refreshed periodically from time to time such as by a firmware upgrade, by replacing a memory card, or via communications link 118. Profile parameters may be analyzed and processed on another computer such as a remote server and periodically sent to patient control module 800.

An example of the patient monitoring system in operation is illustrated in FIG. 9 at 900. At 902, the patient profile is initialized. This may be performed by a caregiver using a computer 106 interacting with a remote server or database. An initial portion of patient information may be retrieved from a remote server and display in a profile generation or initialization interface for the caregiver to edit. The profile initialization interface may also be configured to accept input from a user allowing the user to select a default profile based on default profile options. A user may provide input selecting a profile and making any adjustments to the default values for the profile parameters to match the parameters to that specific patient and the patient's treatment plan. When ready, the patient profile may be sent to a patient monitoring device 108.

At 904, the patient monitoring device with the patient's profile may be activated and "installed" or placed in an appropriate location to monitor the patient's activities. Such appropriate locations include any location suitable for monitoring patient activity such as on or adjacent a patient's head, neck, torso, foot, arm, leg or other area. The monitoring device, or parts thereof, may be installed in a bed, chair, or other supporting structure instead of, or in addition to being mounted on the patient. In one example, the monitoring device may be worn by the patient, and at least one of the sensors may be included in the patient's clothing such as in a sock or gown worn by the patient. It may be advantageous to positon the monitoring device, or any of the sensors associated with it, on a patient's extremity such as in a sock worn on a foot, in an armband worn on the wrist, or on the head, knee, or elbow to name a few other non-limiting examples. Such a position can result in more noticeable changes in position that may be used to more accurately predict when a patient is making movements that may result in a fall.

When activated, the patient monitoring device 108 may begin obtaining sensor output at 906, and comparing the sensor output to the profile parameters at 908. If the output is within the limits of the parameters at 910, the monitoring device continues monitoring sensor readings taken at 906. These sensor readings may be sent to a remote server and/or saved to remote data store, as well as transmitted to a specific computer of computers 106 periodically or continuously, or to all computers 106 who are configured to retrieve them.

When the output for a sensor falls outside the threshold values defined by the parameters in the patient profile, an alert may be triggered at 912. The alert may be sent from alarm module 826 and sent to the appropriate caregiver's computer 106. Details about the alarm may be displayed to the respective caregiver(s). If the alarm is confirmed to be valid at 914, the caregiver may provide input to that effect using computer 106. If the alarm is confirmed to be false at 918, the caregiver may acknowledge this as well using computer 106. The system may update the historical sensor and event related data at 920 allowing for refinements to the profile parameter settings for future profiles to improve and refine the system's overall knowledge of patient behavior, and/or to better avoid false alarms in the future. Adjustments to the profile parameters may also be made by the caregiver and sent to the monitoring device 108 at 922 and the monitoring activities may continue at 906.

Glossary of Definitions and Alternatives

While the invention is illustrated in the drawings and described herein, this disclosure is to be considered as illustrative and not restrictive in character. The present disclosure is exemplary in nature and all changes, equivalents, and modifications that come within the spirit of the invention are included. The detailed description is included herein to discuss aspects of the examples illustrated in the drawings for the purpose of promoting an understanding of the principles of the invention. No limitation of the scope of the invention is thereby intended. Any alterations and further modifications in the described examples, and any further applications of the principles described herein are contemplated as would normally occur to one skilled in the art to which the invention relates. Some examples are disclosed in detail, however some features that may not be relevant may have been left out for the sake of clarity.

Where there are references to publications, patents, and patent applications cited herein, they are understood to be incorporated by reference as if each individual publication, patent, or patent application were specifically and individually indicated to be incorporated by reference and set forth in its entirety herein.

Singular forms "a", "an", "the", and the like include plural referents unless expressly discussed otherwise. As an illustration, references to "a device" or "the device" include one or more of such devices and equivalents thereof.

Directional terms, such as "up", "down", "top" "bottom", "fore", "aft", "lateral", "longitudinal", "radial", "circumferential", etc., are used herein solely for the convenience of the reader in order to aid in the reader's understanding of the illustrated examples. The use of these directional terms does not in any manner limit the described, illustrated, and/or claimed features to a specific direction and/or orientation.

Multiple related items illustrated in the drawings with the same part number which are differentiated by a letter for separate individual instances, may be referred to generally by a distinguishable portion of the full name, and/or by the number alone. For example, if multiple "laterally extending elements" 90A, 90B, 90C, and 90D are illustrated in the drawings, the disclosure may refer to these as "laterally extending elements 90A-90D," or as "laterally extending elements 90," or by a distinguishable portion of the full name such as "elements 90".

The language used in the disclosure are presumed to have only their plain and ordinary meaning, except as explicitly defined below. The words used in the definitions included herein are to only have their plain and ordinary meaning. Such plain and ordinary meaning is inclusive of all consistent dictionary definitions from the most recently published Webster's and Random House dictionaries. As used herein, the following definitions apply to the following terms or to common variations thereof (e.g., singular/plural forms, past/present tenses, etc.):

"Antenna" or "Antenna system" generally refers to an electrical device, or series of devices, in any suitable configuration, that converts electric power into electromagnetic radiation. Such radiation may be either vertically, horizontally, or circularly polarized at any frequency along the electromagnetic spectrum. Antennas transmitting with circular polarity may have either right-handed or left-handed polarization.

In the case of radio waves, an antenna may transmit at frequencies ranging along electromagnetic spectrum from extremely low frequency (ELF) to extremely high frequency (EHF). An antenna or antenna system designed to transmit radio waves may comprise an arrangement of metallic conductors (elements), electrically connected (often through a transmission line) to a receiver or transmitter. An oscillating current of electrons forced through the antenna by a transmitter can create an oscillating magnetic field around the antenna elements, while the charge of the electrons also creates an oscillating electric field along the elements. These time-varying fields radiate away from the antenna into space as a moving transverse electromagnetic field wave. Conversely, during reception, the oscillating electric and magnetic fields of an incoming electromagnetic wave exert force on the electrons in the antenna elements, causing them to move back and forth, creating oscillating currents in the antenna. These currents can then be detected by receivers and processed to retrieve digital or analog signals or data.

Antennas can be designed to transmit and receive radio waves substantially equally in all horizontal directions (omnidirectional antennas), or preferentially in a particular direction (directional or high gain antennas). In the latter case, an antenna may also include additional elements or surfaces which may or may not have any physical electrical connection to the transmitter or receiver. For example, parasitic elements, parabolic reflectors or horns, and other such non-energized elements serve to direct the radio waves into a beam or other desired radiation pattern. Thus antennas may be configured to exhibit increased or decreased directionality or "gain" by the placement of these various surfaces or elements. High gain antennas can be configured to direct a substantially large portion of the radiated electromagnetic energy in a given direction that may be vertical horizontal or any combination thereof.

Antennas may also be configured to radiate electromagnetic energy within a specific range of vertical angles (i.e. "takeoff angles) relative to the earth in order to focus electromagnetic energy toward an upper layer of the atmosphere such as the ionosphere. By directing electromagnetic energy toward the upper atmosphere at a specific angle, specific skip distances may be achieved at particular times of day by transmitting electromagnetic energy at particular frequencies.

Other examples of antennas include emitters and sensors that convert electrical energy into pulses of electromagnetic energy in the visible or invisible light portion of the electromagnetic spectrum. Examples include light emitting diodes, lasers, and the like that are configured to generate electromagnetic energy at frequencies ranging along the electromagnetic spectrum from far infrared to extreme ultraviolet.

"Battery" generally refers to an electrical energy storage device or storage system including multiple energy storage devices. A battery may include one or more separate electrochemical cells, each converting stored chemical energy into electrical energy by a chemical reaction to generate an electromotive force (or "EMF" measured in Volts). An individual battery cell may have a positive terminal (cathode) with a higher electrical potential, and a negative terminal (anode) that is at a lower electrical potential than the cathode. Any suitable electrochemical cell may be used that employ any suitable chemical process, including galvanic cells, electrolytic cells, fuel cells, flow cells and voltaic piles. When a battery is connected to an external circuit, electrolytes are able to move as ions within the battery, allowing the chemical reactions to be completed at the separate terminals thus delivering energy to the external circuit.

A battery may be a "primary" battery that can produce current immediately upon assembly. Examples of this type include alkaline batteries, nickel oxyhydroxide, lithium-copper, lithium-manganese, lithium-iron, lithium-carbon, lithium-thionyl chloride, mercury oxide, magnesium, zinc-air, zinc-chloride, or zinc-carbon batteries. Such batteries are often referred to as "disposable" insofar as they are generally not rechargeable and are discarded or recycled after discharge.

A battery may also be a "secondary" or "rechargeable" battery that can produce little or no current until charged. Examples of this type include lead-acid batteries, valve regulated lead-acid batteries, sealed gel-cell batteries, and various "dry cell" batteries such as nickel-cadmium (NiCd), nickel-zinc (NiZn), nickel metal hydride (NiMH), and lithium-ion (Li-ion) batteries.

"Beacon" or "beacon transmitter" generally refers to a system or apparatus configured to transmit data using electromagnetic energy. The broadcasted data may include any suitable data such as a string of alphanumeric characters uniquely identifying one beacon from others in the environment. Data may appear in a single field in a datagram, or in multiple separate fields. Any suitable protocol may be used to create and transmit the datagrams using any suitable arrangement of fields. The fields may include predetermined numbers of bits according to proprietary or commercially available protocols. One example of a commercially available protocol is the Bluetooth® LE (Low Energy) protocol, also referred to as Bluetooth® Smart protocol.

Datagrams may include one or more fields that may include a preamble, one or more header fields, an access address field, a Cyclical Redundancy Check (CRC) field, a Protocol Data Unit (PDU) field, a Media Access Control (MAC) address field, and a data field. The data field may include an prefix and a proximity Universal Unique Identifier (UUID) which may be configured to distinguish beacons used by one organization from those of another organization. Other data fields may include a major field which may be used to identify multiple beacons as a group, a minor field which may uniquely identify a specific beacon within a group, and a transmission power field which may indicate how far a beacon is from a receiver. The transmitter power field may include one of a set of data values representing distance ranges such as "immediate", "far", or "out of range". A transmission power field may also include more detailed ranging data such as the Received Signal Strength Indication (RSSI) of the beacon at a predetermined range such as 1 meter away. This value may be compared to a current RSSI measured by a receiver and used to calculate an approximate range.

A beacon may include a receiver allowing the beacon to begin broadcasting after receiving a signal from another transmitter. In one example, a beacon may collect energy from the electromagnetic energy directed toward it and may use this energy to transmit its data in response. This type of "passive" beacon may only transmit when energized to do so by some other transmitter. In another example, beacons may have a local power source such as a battery and may transmit continuously and/or at predetermined intervals. In either case, the data sent by the beacon may pass through walls or other objects between the beacon and a receiver making it unnecessary to maintain an unobstructed line of sight between the to.

A beacon may transmit on any suitable frequency or group of frequencies in the electromagnetic spectrum. For example, a beacon may transmit in the Very High Frequency range (VHF), the Ultra High Frequency range (UHF), or in the Super High Frequency range (SHF). Transmissions from a beacon may be directed along a narrow beam by a directional antenna system used by the beacon, or the beacon may use an omnidirectional antenna system configured to broadcast the data in all directions at about the same time.

The data may be programmed in a memory such as a nonvolatile memory in the beacon for repeated transmission at predetermined intervals. For example, transmissions may be repeated up to about every 500 ms, up to about every 2 seconds, up to about every 30 seconds, or at intervals greater than 30 seconds apart. Beacons may transmit at a very low Transmitter Power Output (TPO) and/or Effective Radiated Power (ERP). TPO or ERP may be less than about 100 milliwatts, less than about 10 milliwatts, or less than about 1 milliwatt.

"Circuit" generally refers to one or more conductive wires or traces connecting one or more individual electronic components, such as resistors, transistors, capacitors, inductors, diodes, sensors, lamps, processors, controllers, and the like, through which electric current can flow. Circuit components can be connected by individual pieces of wire or individual traces, or by interconnections created by photolithographic techniques on a laminated substrate (e.g. a Printed Circuit Board or PCB). Circuits can be microscopic and entirely or partially encapsulated in a plastic, ceramic, or other insulative material. Such circuits are commonly referred to as "integrated" circuits (IC). In an integrated circuit or IC, the components and interconnections may be formed on a semiconducting substrate such as silicon or gallium arsenide to name a few examples.

"Communication Link" generally refers to a connection between two or more communicating entities and may or may not include a communications channel between the communicating entities. The communication between the communicating entities may occur by any suitable means. For example the connection may be implemented as an actual physical link, an electrical link, an electromagnetic link, a logical link, or any other suitable linkage facilitating communication.

In the case of an actual physical link, communication may occur by multiple components in the communication link configured to respond to one another by physical movement of one element in relation to another. In the case of an electrical link, the communication link may be composed of multiple electrical conductors electrically connected to form the communication link.

In the case of an electromagnetic link, the connection may be implemented by sending or receiving electromagnetic energy at any suitable frequency, thus allowing communications to pass as electromagnetic waves. These electromagnetic waves may or may not pass through a physical medium such as an optical fiber, or through free space, or any combination thereof. Electromagnetic waves may be passed at any suitable frequency including any frequency in the electromagnetic spectrum.

A communication link may include any suitable combination of hardware which may include software components as well. Such hardware may include routers, switches, networking endpoints, repeaters, signal strength enters, hubs, and the like.

In the case of a logical link, the communication link may be a conceptual linkage between the sender and recipient such as a transmission station in the receiving station. Logical link may include any combination of physical, electrical, electromagnetic, or other types of communication links.

"Communication node" generally refers to a physical or logical connection point, redistribution point or endpoint along a communication link. A physical network node is generally referred to as an active electronic device attached or coupled to a communication link, either physically, logically, or electromagnetically. A physical node is capable of sending, receiving, or forwarding information over a communication link. A communication node may or may not include a computer, processor, transmitter, receiver, repeater, and/or transmission lines, or any combination thereof.

"Computer" generally refers to any computing device configured to compute a result from any number of input values or variables. A computer may include a processor for performing calculations to process input or output. A computer may include a memory for storing values to be processed by the processor, or for storing the results of previous processing.

A computer may also be configured to accept input and output from a wide array of input and output devices for receiving or sending values. Such devices include other computers, keyboards, mice, visual displays, printers, industrial equipment, and systems or machinery of all types and sizes. For example, a computer can control a network or network interface to perform various network communications upon request. The network interface may be part of the computer, or characterized as separate and remote from the computer.

A computer may be a single, physical, computing device such as a desktop computer, a laptop computer, or may be composed of multiple devices of the same type such as a group of servers operating as one device in a networked cluster, or a heterogeneous combination of different computing devices operating as one computer and linked together by a communication network. The communication network connected to the computer may also be connected to a wider network such as the internet. Thus a computer may include one or more physical processors or other computing devices or circuitry, and may also include any suitable type of memory.

A computer may also be a virtual computing platform having an unknown or fluctuating number of physical processors and memories or memory devices. A computer may thus be physically located in one geographical location or physically spread across several widely scattered locations with multiple processors linked together by a communication network to operate as a single computer.

The concept of "computer" and "processor" within a computer or computing device also encompasses any such processor or computing device serving to make calculations or comparisons as part of the disclosed system. Processing operations related to threshold comparisons, rules comparisons, calculations, and the like occurring in a computer may occur, for example, on separate servers, the same server with separate processors, or on a virtual computing environment having an unknown number of physical processors as described above.

A computer may be optionally coupled to one or more visual displays and/or may include an integrated visual display. Likewise, displays may be of the same type, or a heterogeneous combination of different visual devices. A computer may also include one or more operator input devices such as a keyboard, mouse, touch screen, laser or infrared pointing device, or gyroscopic pointing device to name just a few representative examples. Also, besides a display, one or more other output devices may be included such as a printer, plotter, industrial manufacturing machine, 3D printer, and the like. As such, various display, input and output device arrangements are possible.

Multiple computers or computing devices may be configured to communicate with one another or with other devices over wired or wireless communication links to form a network. Network communications may pass through various computers operating as network appliances such as switches, routers, firewalls or other network devices or interfaces before passing over other larger computer networks such as the internet. Communications can also be passed over the network as wireless data transmissions carried over electromagnetic waves through transmission lines or free space. Such communications include using WiFi or other Wireless Local Area Network (WLAN) or a cellular transmitter/receiver to transfer data.

"Data" generally refers to one or more values of qualitative or quantitative variables that are usually the result of measurements. Data may be considered "atomic" as being finite individual units of specific information. Data can also be thought of as a value or set of values that includes a frame of reference indicating some meaning associated with the values. For example, the number "2" alone is a symbol that absent some context is meaningless. The number "2" may be considered "data" when it is understood to indicate, for example, the number of items produced in an hour.

Data may be organized and represented in a structured format. Examples include a tabular representation using rows and columns, a tree representation with a set of nodes considered to have a parent-children relationship, or a graph representation as a set of connected nodes to name a few.

The term "data" can refer to unprocessed data or "raw data" such as a collection of numbers, characters, or other symbols representing individual facts or opinions. Data may be collected by sensors in controlled or uncontrolled environments, or generated by observation, recording, or by processing of other data. The word "data" may be used in a plural or singular form. The older plural form "datum" may be used as well.

"Database" also referred to as a "data store", "data repository", or "knowledge base" generally refers to an organized collection of data. The data is typically organized to model aspects of the real world in a way that supports processes obtaining information about the world from the data. Access to the data is generally provided by a "Database Management System" (DBMS) consisting of an individual computer software program or organized set of software programs that allow user to interact with one or more databases providing access to data stored in the database (although user access restrictions may be put in place to limit access to some portion of the data). The DBMS provides various functions that allow entry, storage and retrieval of large quantities of information as well as ways to manage how that information is organized. A database is not generally portable across different DBMSs, but different DBMSs can interoperate by using standardized protocols and languages such as Structured Query Language (SQL), Open Database Connectivity (ODBC), Java Database Connectivity (JDBC), or Extensible Markup Language (XML) to allow a single application to work with more than one DBMS.

Databases and their corresponding database management systems are often classified according to a particular database model they support. Examples include a DBMS that relies on the "relational model" for storing data, usually referred to as Relational Database Management Systems (RDBMS). Such systems commonly use some variation of SQL to perform functions which include querying, formatting, administering, and updating an RDBMS. Other examples of database models include the "object" model, the "object-relational" model, the "file", "indexed file" or "flat-file" models, the "hierarchical" model, the "network" model, the "document" model, the "XML" model using some variation of XML, the "entity-attribute-value" model, and others.

Examples of commercially available database management systems include PostgreSQL provided by the PostgreSQL Global Development Group; Microsoft SQL Server provided by the Microsoft Corporation of Redmond, Wash., USA; MySQL and various versions of the Oracle DBMS, often referred to as simply "Oracle" both separately offered by the Oracle Corporation of Redwood City, Calif., USA; the DBMS generally referred to as "SAP" provided by SAP SE of Walldorf, Germany; and the DB2 DBMS provided by the International Business Machines Corporation (IBM) of Armonk, N.Y., USA.

The database and the DBMS software may also be referred to collectively as a "database". Similarly, the term "database" may also collectively refer to the database, the corresponding DBMS software, and a physical computer or collection of computers. Thus the term "database" may refer to the data, software for managing the data, and/or a physical computer that includes some or all of the data and/or the software for managing the data.

"Display device" generally refers to any device capable of being controlled by an electronic circuit or processor to display information in a visual or tactile. A display device may be configured as an input device taking input from a user or other system (e.g. a touch sensitive computer screen), or as an output device generating visual or tactile information, or the display device may configured to operate as both an input or output device at the same time, or at different times.

The output may be two-dimensional, three-dimensional, and/or mechanical displays and includes, but is not limited to, the following display technologies: Cathode ray tube display (CRT), Light-emitting diode display (LED), Electroluminescent display (ELD), Electronic paper, Electrophoretic Ink (E-ink), Plasma display panel (PDP), Liquid crystal display (LCD), High-Performance Addressing display (HPA), Thin-film transistor display (TFT), Organic light-emitting diode display (OLED), Surface-conduction electron-emitter display (SED), Laser TV, Carbon nanotubes, Quantum dot display, Interferometric modulator display (IMOD), Swept-volume display, Varifocal mirror display, Emissive volume display, Laser display, Holographic display, Light field displays, Volumetric display, Ticker tape, Split-flap display, Flip-disc display (or flip-dot display), Rollsign, mechanical gauges with moving needles and accompanying indicia, Tactile electronic displays (aka refreshable Braille display), Optacon displays, or any devices that either alone or in combination are configured to provide visual feedback on the status of a system, such as the "check engine" light, a "low altitude" warning light, an array of red, yellow, and green indicators configured to indicate a temperature range.

"Electromagnetic Radiation" generally refers to energy radiated by electromagnetic waves. Electromagnetic radiation is produced from other types of energy, and is converted to other types when it is destroyed. Electromagnetic radiation carries this energy as it travels moving away from its source at the speed of light (in a vacuum). Electromagnetic radiation also carries both momentum and angular momentum. These properties may all be imparted to matter with which the electromagnetic radiation interacts as it moves outwardly away from its source.

Electromagnetic radiation changes speed as it passes from one medium to another. When transitioning from one media to the next, the physical properties of the new medium can cause some or all of the radiated energy to be reflected while the remaining energy passes into the new medium. This occurs at every junction between media that electromagnetic radiation encounters as it travels.

The photon is the quantum of the electromagnetic interaction, and is the basic constituent of all forms of electromagnetic radiation. The quantum nature of light becomes more apparent at high frequencies as electromagnetic radiation behaves more like particles and less like waves as its frequency increases.

"Electromagnetic Waves" generally refers to waves having a separate electrical and a magnetic component. The electrical and magnetic components of an electromagnetic wave oscillate in phase and are always separated by a 90 degree angle. Electromagnetic waves can radiate from a source to create electromagnetic radiation capable of passing through a medium or through a vacuum. Electromagnetic waves include waves oscillating at any frequency in the electromagnetic spectrum including, but not limited to radio waves, visible and invisible light, X-rays, and gamma-rays.

"Input Device" generally refers to any device coupled to a computer that is configured to receive input and deliver the input to a processor, memory, or other part of the computer. Such input devices can include keyboards, mice, trackballs, touch sensitive pointing devices such as touchpads, or touchscreens. Input devices also include any sensor or sensor array for detecting environmental conditions such as temperature, light, noise, vibration, humidity, and the like.

"Location Finding System" generally refers to a system that tracks the location of objects or people in real time. Such systems include space based systems like the Global Positioning System (GPS) which may use a receiver on earth in communication with multiple satellite mounted transmitters in space. Such systems may use time and the known position of the satellites to triangulate a position on earth. The satellites may include accurate clocks that are synchronized to each other and to ground clocks. The satellites may be configured to continuously transmit their current time and position. The ground-based receiver may monitor multiple satellites solving equations in real time to determine the precise position of the receiver. Signals from four satellites may be required for a receiver to make the necessary computations.

In another example sometimes referred to as "Real-time Locating Systems" (RTLS), wireless tags are attached to objects or worn by people. Receivers maintained at known, fixed reference points may receive wireless signals from the tags and use signal strength information to determine their location.

The tags may communicate using electromagnetic energy which may include radio frequency (RF) communication, optical, and/or acoustic technology instead of or in addition to RF communication. Tags and fixed reference points can be transmitters, receivers, or both. Location information may or may not include speed, direction, or spatial orientation, and may in some cases be limited to tracking locations of objects within a building or contained area.

Wireless networking equipment may be engaged as well. In one example, known signal strength readings may be taken in different locations serviced by a wireless network such as in 802.11 Wi-Fi network. These known signal strength readings may be used to calculate or triangulate approximate locations by comparing measured signal strength received from a tag against a stored database of Wi-Fi readings or Received Signal Strength Indicators (RSSI). In this way, one or more probable locations may be indicated a virtual map.

In another example, a wireless network transmitter may be configured to send reference signal strength information in packets or datagrams received by the tags. The tags may be configured to measure and/or calculate the actual signal strength of the signal received from the sending transmitter and compare this actual signal strength to reference signal strength information to determine an approximate distance from the transmitter. This distance information may then be sent to other servers or components in the location finding system and used to triangulate a more precise location for a given tag.

"Memory" generally refers to any storage system or device configured to retain data or information. Each memory may include one or more types of solid-state electronic memory, magnetic memory, or optical memory, just to name a few. Memory may use any suitable storage technology, or combination of storage technologies, and may be volatile, nonvolatile, or a hybrid combination of volatile and nonvolatile varieties. By way of non-limiting example, each memory may include solid-state electronic Random Access Memory (RAM), Sequentially Accessible Memory (SAM) (such as the First-In, First-Out (FIFO) variety or the Last-In-First-Out (LIFO) variety), Programmable Read Only Memory (PROM), Electronically Programmable Read Only Memory (EPROM), or Electrically Erasable Programmable Read Only Memory (EEPROM).

Memory can refer to Dynamic Random Access Memory (DRAM) or any variants, including static random access memory (SRAM), Burst SRAM or Synch Burst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (REDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM).

Memory can also refer to non-volatile storage technologies such as non-volatile read access memory (NVRAM), flash memory, non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Domain Wall Memory (DWM) or "Racetrack" memory, Nano-RAM (NRAM), or Millipede memory. Other non-volatile types of memory include optical disc memory (such as a DVD or CD ROM), a magnetically encoded hard disc or hard disc platter, floppy disc, tape, or cartridge media. The concept of a "memory" includes the use of any suitable storage technology or any combination of storage technologies.

"Module" or "Engine" generally refers to a collection of computational or logic circuits implemented in hardware, or to a series of logic or computational instructions expressed in executable, object, or source code, or any combination thereof, configured to perform tasks or implement processes. A module may be implemented in software maintained in volatile memory in a computer and executed by a processor or other circuit. A module may be implemented as software stored in an erasable/programmable nonvolatile memory and executed by a processor or processors. A module may be implanted as software coded into an Application Specific Information Integrated Circuit (ASIC). A module may be a collection of digital or analog circuits configured to control a machine to generate a desired outcome.

Modules may be executed on a single computer with one or more processors, or by multiple computers with multiple processors coupled together by a network. Separate aspects, computations, or functionality performed by a module may be executed by separate processors on separate computers, by the same processor on the same computer, or by different computers at different times.

"Motion Sensor" generally refers to a device configured to convert physical movement of an object into an electrical or signal. A motion sensor may be thought of as a transducer detecting physical movement and from it producing a signal (e.g. a time varying signal) based on that movement. A motion sensor may operate by detecting changes in its position relative to other objects by emitting and/or detecting electromagnetic waves. Examples include ultrasonic, infrared, video, microwave, or other such motion detectors.

In another example, a motion sensor may operate by detecting changes in the magnitude and direction of proper acceleration caused by gravity ("g-force"). Sometimes called "accelerometers," these motion sensors can detect changes in g-forces on an object as a vector quantity, and can be used to sense changes in orientation (e.g. when the direction of weight changes), coordinate acceleration (e.g. when it produces g-force or a change in g-force), vibration, shock, and/or falling in a resistive medium. An accelerometer may thus be used to detect changes in the position, orientation, and movement of a device.

Commercially available accelerometers include piezoelectric, piezoresistive and capacitive components. Piezoelectric accelerometers may rely on piezoceramics (e.g. lead zirconate titanate) or single crystals (e.g. quartz, tourmaline). Piezoresistive accelerometers may be preferred in high shock applications. Capacitive accelerometers may use a silicon micro-machined sensing element.

A motion sensor may include multiple accelerometers. Some accelerometers are designed to be sensitive only in one direction. A motion sensor sensitive to movement in more than one direction may be constructed by integrating two accelerometers perpendicular to one another within a single package. By adding a third device oriented in a plan orthogonal to two other axes, three axes can be measured.

"Multiple" as used herein is synonymous with the term "plurality" and refers to more than one, or by extension, two or more.

"Network" or "Computer Network" generally refers to a telecommunications network that allows computers to exchange data. Computers can pass data to each other along data connections by transforming data into a collection of datagrams or packets. The connections between computers and the network may be established using either cables, optical fibers, or via electromagnetic transmissions such as for wireless network devices.

Computers coupled to a network may be referred to as "nodes" or as "hosts" and may originate, broadcast, route, or accept data from the network. Nodes can include any computing device such as personal computers, phones, servers as well as specialized computers that operate to maintain the flow of data across the network, referred to as "network devices". Two nodes can be considered "networked together" when one device is able to exchange information with another device, whether or not they have a direct connection to each other.

Examples of wired network connections may include Digital Subscriber Lines (DSL), coaxial cable lines, or optical fiber lines. The wireless connections may include BLUETOOTH, Worldwide Interoperability for Microwave Access (WiMAX), infrared channel or satellite band, or any wireless local area network (Wi-Fi) such as those implemented using the Institute of Electrical and Electronics Engineers' (IEEE) 802.11 standards (e.g. 802.11(a), 802.11 (b), 802.11(g), or 802.11(n) to name a few). Wireless links may also include or use any cellular network standards used to communicate among mobile devices including 1G, 2G, 3G, or 4G. The network standards may qualify as 1G, 2G, etc. by fulfilling a specification or standards such as the specifications maintained by International Telecommunication Union (ITU). For example, a network may be referred to as a "3G network" if it meets the criteria in the International Mobile Telecommunications-2000 (IMT-2000) specification regardless of what it may otherwise be referred to. A network may be referred to as a "4G network" if it meets the requirements of the International Mobile Telecommunications Advanced (IMTAdvanced) specification. Examples of cellular network or other wireless standards include AMPS, GSM, GPRS, UMTS, LTE, LTE Advanced, Mobile WiMAX, and WiMAX-Advanced.

Cellular network standards may use various channel access methods such as FDMA, TDMA, CDMA, or SDMA. Different types of data may be transmitted via different links and standards, or the same types of data may be transmitted via different links and standards.

The geographical scope of the network may vary widely. Examples include a body area network (BAN), a personal area network (PAN), a low power wireless Personal Area Network using IPv6 (6LoWPAN), a local-area network (LAN), a metropolitan area network (MAN), a wide area network (WAN), or the Internet.

A network may have any suitable network topology defining the number and use of the network connections. The network topology may be of any suitable form and may include point-to-point, bus, star, ring, mesh, or tree. A network may be an overlay network which is virtual and is configured as one or more layers that use or "lay on top of" other networks.

A network may utilize different communication protocols or messaging techniques including layers or stacks of protocols. Examples include the Ethernet protocol, the internet protocol suite (TCP/IP), the ATM (Asynchronous Transfer Mode) technique, the SONET (Synchronous Optical Networking) protocol, or the SDE1 (Synchronous Digital Elierarchy) protocol. The TCP/IP internet protocol suite may include application layer, transport layer, internet layer (including, e.g., IPv6), or the link layer.

"Output Device" generally refers to any device or collection of devices that is controlled by computer to produce an output. This includes any system, apparatus, or equipment receiving signals from a computer to control the device to generate or create some type of output. Examples of output devices include, but are not limited to, screens or monitors displaying graphical output, any projector a projecting device projecting a two-dimensional or three-dimensional image, any kind of printer, plotter, or similar device producing either two-dimensional or three-dimensional representations of the output fixed in any tangible medium (e.g. a laser printer printing on paper, a lathe controlled to machine a piece of metal, or a three-dimensional printer producing an object). An output device may also produce intangible output such as, for example, data stored in a database, or electromagnetic energy transmitted through a medium or through free space such as audio produced by a speaker controlled by the computer, radio signals transmitted through free space, or pulses of light passing through a fiber-optic cable.

"Pad" or "patch" generally refers to a thin flat mat or cushion. Examples include a guard worn to shield body parts against abrasion or impact, or to absorb liquids or other viscous materials. Any suitable material may be used in this context as a pad such as plastic, cloth, paper, thin metals, and the like.

As an element in a circuit, a pad or patch generally refers to a small area of electrically conductive material that may be electrically and/or physically connected to a circuit. A pad may allow for physical as well as electrical connection to the circuit such as by allowing a component or trace to be soldered to a Printed Circuit Board (PCB). A patch may refer to a pad that is attached to or incorporated into a fabric such as by weaving conductive threads into a specific predetermined area of the fabric. Pads or patches may be configured as a "surface mount" type with circuits connecting to the pad on the same surface of the board or fabric as the pad, or a "through-hole" type where pins of the components pass through the pad from one side to the other and are soldered, clamped in place, or otherwise maintained in position relative to the pad.

"Piezoresistive Effect" generally refers to an effect caused in Piezoresistive materials where the electrical resistance of the material increases as it is deformed. Examples of Piezoresistive materials include Monocrystalline Silicon, Polysilicon Thin Film, Bonded Metal Foil, Thick Film, and Sputtered Thin Film. Generally, the strain gauges are connected to form a Wheatstone bridge circuit to maximize the output of the sensor and to reduce sensitivity to errors. This is the most commonly employed sensing technology for general purpose pressure measurement.

"Pin" generally refers to a thin piece of material often having a sharpened point at one end for penetrating into and fastening to another material. A pin may have a head opposite the point that is blunt such as in the case of a nail, knitting needle, or sewing pin, or the opposing end of the pin may be attached to another item such as in the case of a pin for an electronic connector mounted to a Printed Circuit Board (PCB). A pin may be made of any suitable material such as copper, aluminum, steel, plastic, wood, and the like. Pins are often elongate structures with circular, ovular, rectangular, triangular, or any other suitable cross section. Examples of pins include nails, staples, tacks, bolts, pegs, rivets, screws, safety pins, sewing needles, or pins in an electronic connector, and the like.

"Personal computing device" generally refers to a computing device configured for use by individual people. Examples include mobile devices such as Personal Digital Assistants (PDAs), tablet computers, wearable computers installed in items worn on the human body such as in eye glasses, watches, laptop computers, portable music/video players, computers in automobiles, or cellular telephones such as smart phones. Personal computing devices can be devices that are typically not mobile such as desk top computers, game consoles, or server computers. Personal computing devices may include any suitable input/output devices and may be configured to access a network such as through a wireless or wired connection, and/or via other network hardware.

"Pressure Sensor" generally refers to a transducer configured to sense or detect a pressure local to the sensor. Types of pressure sensors include, but are not limited to, sensors that measure absolute pressure, gauge pressure, vacuum pressure, or differences between two pressures connected to each side of the sensor (differential sensor).

Any suitable pressure sensing technology may be used including, but not limited to, force collecting sensors which use a diaphragm, piston, bourdon tube, or bellows to measure strain or deflection due to applied force over an area. Examples of the force collector sensor include a Piezoresistive strain gauge which uses the piezoresistive effect of bonded or formed strain gauges to detect strain due to applied pressure. Capacitive pressure sensors use a diaphragm and pressure cavity to create a variable capacitor to detect strain due to applied pressure, capacitance decreasing as pressure deforms the diaphragm. Common technologies use metal, ceramic, and silicon diaphragms. Electromagnetic pressure sensors measure the displacement of a diaphragm by measuring changes in inductance (reluctance), measuring changes in a position as measured by a Linear Variable Differential Transformer (LVDT), measuring changes in a Hall Effect, or by measuring changes in electrical current caused by eddy currents to name a few examples. Piezoelectric pressure sensors use the piezoelectric effect in certain materials such as quartz to measure the strain upon the sensing mechanism due to pressure. Optical pressure sensors include those that use the physical change of an optical fiber to detect strain due to applied pressure. Some examples of this type utilize Fiber Bragg Gratings. Another analogous technique utilizes an elastic film constructed in layers that can change reflected wavelengths according to the applied pressure. Potentiometric pressure sensors use the motion of a wiper along a resistive mechanism to detect the strain caused by applied pressure.

Other types of pressure sensors may use other properties (such as density) to infer pressure of a gas, or liquid. For example some pressure sensors may use the changes in a resonant frequency in a sensing mechanism to measure stress, or changes in gas density, caused by applied pressure. This technology may be used in conjunction with other types of sensors such as force collectors discussed above. Alternatively, resonant technology may be employed by exposing the resonating element itself to the media, whereby the resonant frequency is dependent upon the density of the media. Sensors have been made out of vibrating wire, vibrating cylinders, quartz, and silicon MEMS. In another example, pressure sensors such as the Pirani gauge may use changes in thermal conductivity of a gas due to density changes to measure pressure. The pressure sensor such as a Hot And Cold Cathode gauge may also measure the flow of charged gas particles (ions) which varies due to density changes to measure pressure.

"Processor" generally refers to one or more electronic components configured to operate as a single unit configured or programmed to process input to generate an output. Alternatively, when of a multi-component form, a processor may have one or more components located remotely relative to the others. One or more components of each processor may be of the electronic variety defining digital circuitry, analog circuitry, or both. In one example, each processor is of a conventional, integrated circuit microprocessor arrangement, such as one or more PENTIUM, i3, i5 or i7 processors supplied by INTEL Corporation of Santa Clara, Calif., USA. Other examples of commercially available processors include but are not limited to the X8 and Freescale Coldfire processors made by Motorola Corporation of Schaumburg, Illinois, USA; the ARM processor and TEGRA System on a Chip (SoC) processors manufactured by Nvidia of Santa Clara, Calif., USA; the POWER7 processor manufactured by International Business Machines of White Plains, N.Y., USA; any of the FX, Phenom, Athlon, Sempron, or Opteron processors manufactured by Advanced Micro Devices of Sunnyvale, Calif., USA; or the Snapdragon SoC processors manufactured by Qalcomm of San Diego, Calif., USA.

A processor also includes Application-Specific Integrated Circuit (ASIC). An ASIC is an Integrated Circuit (IC) customized to perform a specific series of logical operations is controlling a computer to perform specific tasks or functions. An ASIC is an example of a processor for a special purpose computer, rather than a processor configured for general-purpose use. An application-specific integrated circuit generally is not reprogrammable to perform other functions and may be programmed once when it is manufactured.

In another example, a processor may be of the "field programmable" type. Such processors may be programmed multiple times "in the field" to perform various specialized or general functions after they are manufactured. A field-programmable processor may include a Field-Programmable Gate Array (FPGA) in an integrated circuit in the processor. FPGA may be programmed to perform a specific series of instructions which may be retained in nonvolatile memory cells in the FPGA. The FPGA may be configured by a customer or a designer using a hardware description language (HDL). In FPGA may be reprogrammed using another computer to reconfigure the FPGA to implement a new set of commands or operating instructions. Such an operation may be executed in any suitable means such as by a firmware upgrade to the processor circuitry.

Just as the concept of a computer is not limited to a single physical device in a single location, so also the concept of a "processor" is not limited to a single physical logic circuit or package of circuits but includes one or more such circuits or circuit packages possibly contained within or across multiple computers in numerous physical locations. In a virtual computing environment, an unknown number of physical processors may be actively processing data, the unknown number may automatically change over time as well.

The concept of a "processor" includes a device configured or programmed to make threshold comparisons, rules comparisons, calculations, or perform logical operations applying a rule to data yielding a logical result (e.g. "true" or "false"). Processing activities may occur in multiple single processors on separate servers, on multiple processors in a single server with separate processors, or on multiple processors physically remote from one another in separate computing devices.

"Proximity Sensor" generally refers to a sensor configured to generate a signal based on distance to a nearby object, or "target", generally without requiring physical contact. Lack of mechanical physical contact between the sensor and the sensed object provides the opportunity for extra reliability and long functional life.

A proximity sensor may emit an electromagnetic field or a beam of electromagnetic radiation (e.g. infrared light, for instance), and the sensor may determine proximity based on changes in the field or return signal. The object being sensed is often referred to as the "target" or "sensor target". Different proximity targets demand different sensors. For example, a capacitive or photoelectric sensor might be suitable for a plastic target; an inductive proximity sensor may require a metallic target.

The maximum distance that a proximity sensor can detect the target is defined as the sensor's "nominal range". A sensor may begin to emit a signal, or may change the signal already emitted when the distance from the target to the sensor exceeds the nominal range. Some sensors allow for adjustments to the nominal range, or may be configured to return an analog or digital time varying signal based on changes on the distance to the target in time.

"Receive" generally refer system be sent to the monitoring system s to accepting something transferred, communicated, conveyed, relayed, dispatched, or forwarded. The concept may or may not include the act of listening or waiting for something to arrive from a transmitting entity. For example, a transmission may be received without knowledge as to who or what transmitted it. Likewise the transmission may be sent with or without knowledge of who or what is receiving it. To "receive" may include, but is not limited to, the act of capturing or obtaining electromagnetic energy at any suitable frequency in the electromagnetic spectrum. Receiving may occur by sensing electromagnetic radiation. Sensing electromagnetic radiation may involve detecting energy waves moving through or from a medium such as a wire or optical fiber. Receiving includes receiving digital signals which may define various types of analog or binary data such as signals, datagrams, packets and the like.

"Receiver" generally refers to a device configured to receive, for example, digital or analog signals carrying information via electromagnetic energy. A receiver using electromagnetic energy may operate with an antenna or antenna system to intercept electromagnetic waves passing through a medium such as air, a conductor such as a metallic cable, or through glass fibers. A receiver can be a separate piece of electronic equipment, or an electrical circuit within another electronic device. A receiver and a transmitter combined in one unit are called a "transceiver".

A receiver may use electronic circuits configured to filter or separate one or more desired radio frequency signals from all the other signals received by the antenna, an electronic amplifier to increase the power of the signal for further processing, and circuits configured to demodulate the information received.

Examples of the information received include sound (an audio signal), images (a video to signal) or data (a digital signal). Devices that contain radio receivers include television sets, radar equipment, two-way radios, cell phones and other cellular devices, wireless computer networks, GPS navigation devices, radio telescopes, Bluetooth enabled devices, garage door openers, and/or baby monitors.

"Rule" generally refers to a conditional statement with at least two outcomes. A rule may be compared to available data which can yield a positive result (all aspects of the conditional statement of the rule are satisfied by the data), or a negative result (at least one aspect of the conditional statement of the rule is not satisfied by the data). One example of a rule is shown below as pseudo code of an "if/then/else" statement that may be coded in a programming language and executed by a processor in a computer:

```
if(clouds.areGrey( ) and
    (clouds.numberOfClouds > 100)) then {
        prepare for rain;
} else {
        Prepare for sunshine;
}
```

"Sensor" generally refers to a transducer configured to sense or detect a characteristic of the environment local to the sensor. For example, sensors may be constructed to detect events or changes in quantities or sensed parameters providing a corresponding output, generally as an electrical or electromagnetic signal. A sensor's sensitivity indicates how much the sensor's output changes when the input quantity being measured changes.

"Sense parameter" generally refers to a property of the environment detectable by a sensor. As used herein, sense parameter can be synonymous with an operating condition, environmental factor, sensor parameter, or environmental condition. Sense parameters may include temperature, air pressure, speed, acceleration, the presence or intensity of sound or light or other electromagnetic phenomenon, the strength and/or orientation of a magnetic or electrical field, and the like.

"Short Message Service (SMS)" generally refers to a text messaging service component of phone, Web, or mobile communication systems. It uses standardized communications protocols to allow fixed line or mobile phone devices to exchange short text messages. Transmission of short messages between a Short Message Service Center (SMSC) and personal computing device is done whenever using the Mobile Application Part (MAP) of the SS7 protocol. Messages payloads may be limited by the constraints of the signaling protocol to precisely 140 octets (140 octets * 8 bits/octet=1120 bits). Short messages can be encoded using a variety of alphabets: the default GSM 7-bit alphabet, the 8-bit data alphabet, and the 16-bit UCS-2 alphabet. Depending on which alphabet the subscriber has configured in the handset, this leads to the maximum individual short message sizes of 160 7-bit characters, 140 8-bit characters, or 70 16-bit characters.

"Trace" or "track" generally refers to a conductive pathway in an electrical circuit that allows electricity to flow from one electronic device to another. Examples include lines of conductive material in a Printed Circuit Board (PCB) interconnecting components mounted to the PCB such as processors, memory, diodes, resistors, LEDs, and the like. Traces may include any suitable conductive material such as aluminum, or copper. Traces may be microscopic in size such as in the case of a microchip. Micro-sized traces used in this context are sometimes referred to as "tracks."

"Transmit" generally refers to causing something to be transferred, communicated, conveyed, relayed, dispatched, or forwarded. The concept may or may not include the act of conveying something from a transmitting entity to a receiving entity. For example, a transmission may be received without knowledge as to who or what transmitted it. Likewise the transmission may be sent with or without knowledge of who or what is receiving it. To "transmit" may include, but is not limited to, the act of sending or broadcasting electromagnetic energy at any suitable frequency in the electromagnetic spectrum. Transmissions may include digital signals which may define various types of binary data such as datagrams, packets and the like. A transmission may also include analog signals.

Information such as a signal provided to the transmitter may be encoded or modulated by the transmitter using various digital or analog circuits. The information may then be transmitted. Examples of such information include sound (an audio signal), images (a video signal) or data (a digital signal). Devices that contain radio transmitters include radar equipment, two-way radios, cell phones and other cellular devices, wireless computer networks and network devices, GPS navigation devices, radio telescopes, Radio Frequency Identification (RFID) chips, Bluetooth enabled devices, and garage door openers.

"Transmitter" generally refers to a device configured to transmit, for example, digital or analog signals carrying information via electromagnetic energy. A transmitter using electromagnetic energy may operate with an antenna or antenna system to produce electromagnetic waves passing through a medium such as air, a conductor such as a metallic cable, or through glass fibers. A transmitter can be a separate piece of electronic equipment, or an electrical circuit within another electronic device. A transmitter and a receiver combined in one unit are called a "transceiver".

"Triggering a Rule" generally refers to an outcome that follows when all elements of a conditional statement expressed in a rule are satisfied. In this context, a conditional statement may result in either a positive result (all conditions of the rule are satisfied by the data), or a negative result (at least one of the conditions of the rule is not satisfied by the data) when compared to available data. The conditions expressed in the rule are triggered if all conditions are met causing program execution to proceed along a different path than if the rule is not triggered.

What is claimed is:

1. A mounting assembly, comprising:
   a sock having fabric, the sock adapted for a foot of a patient;
   one or more pressure sensors adapted and arranged to detect pressure applied by the foot, wherein one or more pressure sensors are included in the fabric of the sock; and
   a pad and a frame capturing a portion of the sock between the pad positioned on a first side of the fabric, and the frame positioned on a second side of the fabric, the pad having one or more pins extending through the fabric and into at least a portion of the frame, wherein at least one of the pins is electrically connected to at least one of the pressure sensors of the sock.

2. The mounting assembly of claim 1, wherein the fabric includes conductive traces electrically connected to the one or more pressure sensors.

3. The mounting assembly of claim 2, wherein at least one of the one or more pins of the pad passes through one of the conductive traces.

4. The mounting assembly of claim 1, wherein at least one of the pressure sensors includes one or more resistive threads woven into the fabric, and wherein the resistive threads change resistance according to pressure applied to the sock.

5. The mounting assembly of claim 2, wherein the pad includes one or more pins extending through the fabric and into at least a portion of the frame, and wherein the pins are electrically connected to at least one of the conductive traces.

6. The mounting assembly of claim 5, wherein the frame has one or more electrically conductive terminals electrically connected to at least one of the pins of the pad.

7. The mounting assembly of claim 1, comprising:
   a control module mounted to the frame, the control module including:
      a processor electrically connected to at least one of the pins that is electrically connected to at least one of the pressure sensors;
      a transmitter, wherein the processor is configured to use the transmitter to transmit signals representing changes in pressure applied to the sock.

8. The mounting assembly of claim 1, wherein the pad and frame are positioned on the sock adjacent an ankle of the foot.

9. The mounting assembly of claim 1, wherein the pad includes one or more retention members, and wherein the frame includes pad mounting receptacles that receive and accept the retention members of the pad that extend through the fabric to engage the pad mounting receptacles.

10. The mounting assembly of claim 7, wherein the frame further comprises:
   one or more engagement members within a central opening defined by the base;
   wherein the control module includes corresponding flanges configured to engage the engagement members; and
   wherein at least a portion of the control module extends into the central opening.

11. The mounting assembly of claim 7, comprising:
   a gyroscope sensor electrically connected to the processor and adapted to detect changes in angular velocity of the sock along three separate axes; and
   an accelerometer electrically connected to the processor and adapted to detect changes in acceleration of the sock along the three separate axes.

12. The mounting assembly of claim 11, the control module further comprising:
   a memory for storing a patient profile;
   wherein the processor activates the gyroscope sensor and begins measuring changes reported by the one or more pressure sensors when changes in acceleration measured by the accelerometer exceed a predetermined activation threshold maintained in the patient profile; and wherein the control module is configured to calculate a triggering value by combining changes in at least the resistance of the resistive threads, the angular velocity, and the acceleration; and wherein the control module is configured to send an alert message via a computer network if the triggering value exceeds a predetermined alert threshold maintained by the patient profile.

13. The mounting assembly of claim 7, the control module further comprising:
a proximity sensor configured to determine a distance between the proximity sensor and a sensor target, wherein the proximity sensor is configured to generate range data based on the distance to the sensor target.

14. The mounting assembly of claim 7, the control module further comprising:
a temperature sensor configured to detect changes in a body temperature of the patient, or changes in an environmental temperature of the environment around the patient.

15. The mounting assembly of claim 1, wherein the fabric is free of electrical terminals mounted to the fabric that extend outwardly away from the sock.

16. A mounting assembly, comprising:
a pad having one or more pins extending through fabric of a garment from inside to outside, wherein the fabric includes at least one electrical circuit that includes at least one pressure sensor, and wherein at least one of the pins is electrically connected by the fabric to at least one electrical circuit; and
a base outside of the garment having and one or more sensor terminals in electrical connection with one or more receptacles defined by the base arranged to receive the pins extending through the fabric, and wherein the pins are removably retained by the receptacles of the base.

17. The mounting assembly of claim 16, comprising:
a control module mounted to the base, the control module having a transmitter and a processor, and one or more control module terminals electrically connect to corresponding sensor terminals of the pad, wherein the processor is configured to control the transmitter to transmit signals representing changes in pressure detected by the pressure sensor.

18. The mounting assembly of claim 16, wherein at least one of the pressure sensors includes has piezoelectric threads woven into the fabric of the garment arranged and adapted to change resistance as pressure is applied to the piezoelectric threads.

19. The mounting assembly of claim 16, wherein the electrical circuit includes conductive threads woven into the fabric of the garment electrically connecting the at least one pressure sensor to the one or more pins.

20. The mounting assembly of claim 16, the pressure sensor included with the garment has a sensor thickness that is less than or equal to a fabric thickness of the fabric.

21. The mounting assembly of claim 16, wherein the garment is a sock for a patient's foot, and wherein the pad and base are positioned on the sock adjacent a heel of the patient.

22. The mounting assembly of claim 17, wherein the base further comprises:
one or more engagement members extending into a central opening defined by the base;
wherein the control module includes flanges configured to engage the engagement members of the base.

23. The mounting assembly of claim 17, the control module further comprising:
a memory for storing a patient profile;
a gyroscope sensor and an accelerometer, wherein the control module activates the gyroscope sensor and the at least one pressure sensor when changes in acceleration measured by the accelerometer exceed a predetermined activation threshold maintained in the patient profile.

24. The mounting assembly of claim 23, wherein the control module is configured to calculate a triggering value by combining changes in at least an angular velocity measured by the gyroscope sensor, and acceleration measured by the accelerometer, and wherein the processor is configured to send an alert message via a computer network if the triggering value exceeds a predetermined alert threshold maintained by the patient profile.

25. The mounting assembly of claim 16, wherein the fabric is free of electrical terminals mounted to the fabric that extend outwardly away from the garment.

* * * * *